(12) United States Patent
Zhang et al.

(10) Patent No.: US 7,563,589 B2
(45) Date of Patent: Jul. 21, 2009

(54) RECONSTITUTED HISTONE METHYLTRANSFERASE COMPLEX AND METHODS OF IDENTIFYING MODULATORS THEREOF

(75) Inventors: Yi Zhang, Chapel Hill, NC (US); Ru Cao, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 11/140,659

(22) Filed: May 27, 2005

(65) Prior Publication Data

US 2005/0266473 A1 Dec. 1, 2005

Related U.S. Application Data

(60) Provisional application No. 60/575,880, filed on Jun. 1, 2004.

(51) Int. Cl.
*C12Q 1/48* (2006.01)
*C12N 9/10* (2006.01)
(52) U.S. Cl. .......................... 435/15; 435/193; 435/325
(58) Field of Classification Search .................. 435/6, 435/193, 348, 69.1, 320.1, 15; 536/23.2
See application file for complete search history.

(56) References Cited

U.S. PATENT DOCUMENTS 6,689,583 B1    2/2004   Jenuwein et al.

FOREIGN PATENT DOCUMENTS

WO    WO 2005/034845 A2    4/2005

OTHER PUBLICATIONS

Cao et al., "SUZ12 is Required for Both the Histone Methyltransferase Activity and the Silencing Function of the EED-EZH2 Complex," *Molecular Cell*, 2004, vol. 15, p. 57-67.
Cao et al., "Role of Histone H3 Lysine 27 Methylation in Polycomb-Group Silencing," *Science*, 2002, vol. 298, p. 1039-1043.
Cao et al., "The Functions of E(Z)/EZH2-mediated methylation of lysine 27 in histone H3," *Current Opinion in Genetics & Development*, 2004, vol. 14, p. 155-164.
Fang et al., "Purification of Histone Methyltransferases from HeLa Cells," *Methods in Enzymology*, vol. 377, p. 213-226.
Muller et al., "Histone Methyltransferase Activity of a *Drosophila* Polycomb Group Repressor Complex," *Cell*, 2002, vol. 111, p. 197-208.
International Search Report and the Written Opinion of the International Searching Authority for PCT Application No. PCT/US05/018840 dated Apr. 12, 2006.
"69th Cold Spring Harbor Symposium on Quantitative Biology: Epigenetics, Jun. 2-7, 2004" <http://meetings.cshl.edu/2004/2004symp.htm> (2004).
Zhang "hDOT1L, a Histone Methyltransferase without a SET Domain, is Involved in Leukemogenesis" slides from oral presentation *28th Linehenger Cancer Symposium "Epigenetcis, chromatin and cancer"* (Apr. 2004).
Zhang "Role of Histone Mehtylation and Ubiquitination in PcG Silencing" slides from oral presentation *Cold Spring Harbor 69th Symposium: Epigenetics* (Jun. 2004).
Zhang "Role of Histone Modification in Polycomb Silencing and Cellular Memory" abstract submitted to the *Cold Spring Harbor 69th Symposium: Epigenetics* (Jun. 2004).
Bannister et al., "Selective Recognition of Methylated Lysine 9 on Histone H3 by the HP1 Chromo Domain" *Nature* 410: 120-124 (2001).
Beisel et al. "Histone Methylation by the *Drosophila* Epigenetic Transcriptional Regulator Ash1" *Nature* 419: 857-862 (2002).
Birve et al. "Su(Z)12, A Novel Drosophila Polycomb Group Gene That Is Conserved In Vertebrates And Plants" *Development* 128: 3371-3379 (2001).
Bracken et al., "EZH2 is Downstream of the pRB-E2F Pathway, Essential for Proliferation and Amplified in Cancer" *The EMBO Journal* 22(20): 5323-5335 (2003).
Cao et al. "Role of Histone H3 Lysine 27 Methylation in Polycomb-Group Silencing" *Science* 298: 1039-1043 (2002).
Cao et al. "SUZ12 is Required for Both the Histone Methyltransferase Activity and the Silencing Function of the EED-EZH2 Complex" *Molecular Cell* 15: 57-67 (2004).
Cao et al., "The Functions of E(Z)EZH1-Mediated Methylation of Lysine 27 in Histone H3" *Current Opinion in Genetics & Development* 14: 155-164 (2004).
Chen et al. "Cloning Of A Human Homolog Of The Drosophila Enhancer Of Zesta Gene (EZH2) That Maps To Chromosome 21q22. 2" *Genomics* 38(1): 30-37 (1996).
Czermin et al. "*Drosophila* Enhancer of Zest/ESC Complexes Have a Histone H3 Methyltransferase Activity that Marks Chromosomal Polycomb Sites" *Cell* 111: 185-196 (2002).
Erhardt et al. "Consequence of the Depletion of Zygotic and Embryonic Enhancer of Zeste 2 During Preimplantation Mouse Development" *Development* 130: 4235-4248 (2003).
Fang et al. "Purification of Histone Methyltransferase from HeLa Cells" *Methods in Enzymology* 377: 213-226 (2004).
Feng et al. "Methylation of H3-Lysine 79 is Mediated by a New Family of HMTases without a SET Domain" *Current Biology* 12: 1052-1058 (2002).
Feng et al. "The NuRD Complex: Linking Histone Modification to Nucleosome Remodeling" *Current Topics in Microbiology and Immunology* 274: 269-290 (2003).

(Continued)

*Primary Examiner*—Nashaat T Nashed
*Assistant Examiner*—Iqbal H Chowdhury
(74) *Attorney, Agent, or Firm*—Myers Bigel Sibley & Sajovec, PA

(57) ABSTRACT

The present invention provides a reconstituted complex including EED, EZH2 and SUZ12 wherein the reconstituted complex has histone methyltransferase (HMTase) activity for lysine 27 of histone H3 (H3-K27). The reconstituted complex may further include RbAp48, AEBP2 or both. Also disclosed are methods of producing the reconstituted complex, methods of identifying compounds that inhibit the HTMase activity of the reconstituted complex and methods of identifying candidate compounds for treating cancer. Reagents and kits including the reconstituted complex are further provided.

15 Claims, 11 Drawing Sheets

OTHER PUBLICATIONS

Fischle et al. "Molecular Basis for the Discrimination of Repressive Methyl-Lysine Marks in Histone H3 Polycomb and HP1 Chromodomains" *Genes & Development* 17: 1870-1881 (2003).

Francis et al. "Mechanisms of Transcriptional Memory" *Nature Reviews: Molecular Cell Biology* 2: 409-421 (2001).

Francis et al. "Reconstitution of a Functional Core Polycomb Repressive Complex" *Molecular Cell* 8:545-556 (2001).

He et al. "Cloning And Characterization Of A Novel Zinc Finger Transcriptional Repressor. A Direct Role Of The Zinc Finger Motif in Repression" *Journal of Biological Chemistry* 274(21): 14678-14684 (1999).

Im et al. "Dynamic Regulation of Histone H3 Methylated at Lusine 79 Within a Tissue-Specific Chromatin Domain" *The Journal of Biological Chemistry* 278(20): 18346-18352 (2003).

Kirmizis et al. "Identification of the Polycomb Group Protein SU(Z)12 as a Potential Molecular Target for Human Therapy" *Molecular Cancer Therapeutics* 2: 113-121 (2003).

Kleer et al. "EZH2 is a Marker of Aggressive Breast Cancer and Promotes Neoplastic Transformation of Breast Epithelial Cells" *Proceedings of the National Academy of Sciences, U.S.A.* 100(20): 11606-11611 (2003).

Kuzmichev et al "Histone Methyltransferase Activity Associated with a Human Multiprotein complex Containing the Enhancer of Zeste Protein" *Genes & Development* 16: 2893-2905 (2002).

Kuzmichev et al. "Different Exh2-Containing Complexes Target Methylation of Histone H1 or Nucleosomal Histone H3" *Molecular Cell* 14:183-193 (2004).

Lachner et al. "Methylation of Histone H3 Lysine 9 Creates a Binding Site for HP1 Proteins" *Nature* 410: 116-120 (2001).

Milne et al. "MLL Targets SET Domain Methyltransferase Activity to *Hox* Gene Promoters" *Molecular Cell* 10: 1107-1117 (2002).

Min et al. "Structural Basis for Specific Binding of Polycomb Chromodomain to Histone H3 Methylated at Lys 27" *Genes & Development* 17: 1823-1828 (2003).

Müller et al. "Histone Methyltransferase Activity of a Drosophila Polycomb Group Repressor Complex" *Cell* 111: 197-208 (2002).

Nakamura et al. "ALL-1 is a Histone Methyltransferase that Assembles a Supercomplex of Proteins Involved in Transcriptional Regulation" *Molecular Cell* 10: 1119-1128 (2002).

Nakayama et al "Role of Histone H3 Lysine 9 Methylation in Epigenetic Control of Heterochromatin Assembly" *Science* 292: 110-113 (2001).

Otte and Kwaks "Gene Repression by Polycomb Group Protein Complexes: A Distinct Complex for Every Occasion?" *Current Opinion in Genetics & Development* 13: 448-454 (2003).

Peters et al. "Partitioning and Plasticity of Repressive Histone Methylation States in Mammalian Chromatin" *Molecular Cell* 12: 1577-1589 (2003).

Plath et al. "Role of Histone H3 Lysine 27 Methylation in X Inactivation" *Science* 300: 131-135 (2003).

Qian et al. "A Retinoblastoma-Binding Protein Related to a Negative Regulator Of Ras in Yeast" *Nature* 264: 648-652 (1993).

Ramsden and Zhang "Everything is E(Z): Linking Histone Methylation to B Cell Development" *Nature Immunology* 4(2): 101-103 (2003).

Rea et al. "Regulation of Chromatin Structure by Site-Specific Histone H3 Methyltransferases" *Nature* 406: 593-599 (2000).

Schumacher et al. "The Murine Polycomb-Group Gene Eed And Its Human Orthologue: Functional Inplications Of Evolutionary Conservation" *Genomics* 54(1): 79-88 (1998).

Sewalt, et al. "Characterization of Interaction Between the Mammalian Polycomb-Group Proteins Enx1/EZH2 and EED Suggests the Existence of Different Mammalian Polycomb-Group Protein Complexes" *Molecular and Cellular Biology* 18(6): 3586-3595 (1998).

Silva et al. "Establishment of Histone H3 Methylation on the Inactive X Chromosome Requires Transient Recruitment of Eed-Enx1 Polycomb Group Complexes" *Developmental Cell* 4: 481-495 (2003).

Simon et al. "Programming Off and On States in Chromatin: Mechanisms of Polycomb and Trithorax Group Complexes" *Current Opinion in Genetics and Development* 12: 210-218 (2002).

Su et al. "Exh2 Controls B Cell Development Through Histone H3 Methylation and *Igh* Rearrangement" *Nature Immunology* 4(2): 124-131 (2003).

VanLohuizen et al. "Interaction of Mouse Polycomb-Group (Pc-G) Proteins Enx1 and Enx2 with Eed: Indication for Separate Pc-G Complexes" *Molecular and Cellular Biology* 18(6): 3572-3579 (1998).

Varambally et al. "The Polycomb Group Protein EXH2 is Involved in Progression of Prostate Cancer" *Nature* 419: 624-629 (2002).

Wang et al. "mAM Facilitates Conversion by ESET of Dimethyl to Trimethyl Lysine 9 of Histone H3 to Cause Transcriptional Repression" *Molecular Cell* 12(2): 475-487 (2003).

Wang et al. "Methylation of Histone H4 at Arginine 3 Facilitating Transcriptional Activation by Nuclear Hormone Receptor" *Science* 293L 853-857 (2001).

Wang et al. "Purification and Functional Characterization of a Histone H3-Lysine 4-Specific Methyltransferase" *Molecular Cell* 8: 120-1217 (2001).

Zhang et al. "Analysis of the NuRD Subunits Reveals a Histone Deacetylase Core Complex and a Connection with DNA Methylation" *Genes and Development* 13: 1924-1935 (1999).

Zhang et al. "Transcription Regulation by Histone Methylation: Interplay Between Different Covalent Modifications of the Core Histone Tails" *Genes and Development* 15: 2343-2360 (2001).

Zhang et al. (Oral and Poster Presentations) "Role of histone methylation and ubiquitination in PcG silencing," Cold Spring Harbor 69th Symposium: Epigenetics, Cold Spring Harbor, NY, USA (Jun. 2-7, 2004).

Zhang, Yi, (Oral Presentation) "hDOT1L, a histone methyltransferase without a SET domain is Involved in leukemogenesis," 528th Lineberger Cancer Symposium, "Epigenetics, Chromatin and Cancer," UNC-CH, Chapel Hill, NC, USA (Apr. 20, 2004).

Zhang, Yi (Oral Presentation) "Role of Histone Methylation in Gene Expression and Cancer," American Association for Cancer Research, Orlando, FL, USA (Mar. 28, 2004).

GenBank Accession No. NM_058083; *Drosophila melanogaster* CG14941-PA (esc) mRNA, complete cds; Source: *Drosophila melanogaster*; Nov. 27, 2001.

GenBank Accession No. NM_079297; *Drosophila melanogaster* CG6502-PA (e(z)) mRNA, complete cds; Source: *Drosophila melanogaster*; Dec. 13, 2001.

GenBank Accession No. NP_003788; embryonic ectoderm development isoform a; Source: *Homo sapiens*; Jun. 22, 2001.

GenBank Accession No. NP_004447; enhancer of zeste 2 isoforms a; Source: *Homo sapiens*; May 7, 1999.

GenBank Accession No. NP_005601; retinoblastoma binding protein 4; Source: *Homo sapiens*; Jun. 10, 1999.

GenBank Accession No. NP_056170l joined to JAZF1; Source: *Homo sapiens*; Apr. 26, 2000.

GenBank Accession No. NP_477431l CG14941-PA; Source: *Drosophila melanogaster*; Nov. 27, 2001.

GenBank Accession No. NP_524021; CG6502-PA; Source: *Drosophila melanogaster*; Dec. 13, 2001.

GenBank Accession No. NP_652059; CG8013-PA Isoform A; Source *Drosophila melanogaster*; Jun. 8, 2002.

GenBank Accession No. NP_694536; embryonic ectoderm development isoform b; Source: *Homo sapiens*; Oct. 16, 2002.

GenBank Accession No. NP_694543; enhancer of zeste 2 isoforms b; Source: *Homo sapiens*; Oct. 7, 2002.

GenBank Accession No. NP_694939; AE binding protein 2; Source: *Homo sapiens*; Oct. 1, 2002.

GenBank Accession No. NP_730465; CG8013-PB Isoform B; Source: *Drosophila melanogaster*; Nov. 6, 2002.

GenBank Accession No. NM_003797; *Homo sapiens* embryonic ectoderm development (EED), transcript varient 1, mRNA; Source: *Homo sapiens*; Jun. 22, 2001.

GenBank Accession No. NM_005610; *Homo sapiens* retinoblastoma binding protein 4 (RBBP4) mRNA; Source: *Homo sapiens*; Jun. 10, 1999.

GenBank Accession No. NM_143802; *Drosophila melanogaster* CG8013-PA, isoform A (Su(z)12) mRNA, complete cds; Source: *Drosophila melanogaster*, Jun. 8, 2002.

GenBank Accession No. NM_152991; *Homo sapiens* embryonic ectoderm development (EED), transcript varient 2, mRNA; Source: *Homo sapiens*; Oct. 16, 2002.

GenBank Accession No. NM_153207; *Homo sapiens* AE binding protein 2(AEBP2) mRNA; Source: *Homo sapiens*; Oct. 1, 2002.

GenBank Accession No. NM_168826; *Drosophila melanogaster* CB8013-PB, isoform B (Su(z)12) mRNA, complete cds; Source: *Drosophila melanogaster*; Nov. 6, 2002.

Jones, et al., The Drosophila esc and E (z) Proteins Are Direct Partners in Polycomb Group-Mediated Repression, *Molecular and Cellular Biology*, May 1998, p. 2825-2834.

Ketel, et al. Subunit Contributions to Histone Methyltransferase Activities of Fly and Worm Polycomb Group Complexes, *Molecular and Cellular Biology*, Aug. 2005, 9. 6857-6868.

Yamamoto, et al., Polycomb Group Suppressor of Zeste 12 Links Heterochromatin Protein 1 and Enchancer of Zeste 2*, *The Journal of Biological Chemistry*, vol. 279, Issue of Jan. 2, pp. 401-406, 2004.

Denisenko et al., "The Product of the Murine Homolog of the *Drosophila extra sex combs* Gene Displays Transcriptional Repressor Activity," *Molecular and Cellular Biology* 17(8): 4707-4717 (1997).

Laible et al., "Mammalian homologues of the *Polycomb*-group gene *Enhancer of zeste* mediate gene silencing in *Drosophila* heterochromatin and at *S.cerevisiae* telomeres," *The EMBO Journal* 16(11): 3219:3232 (1997).

Ringrose et al., "Epigenetic Regulation of Cellular Memory by the Polycomb and Trithorax Group Proteins," *Annu. Rev. Genet.* 38:413-43 (2004).

NCBI Accession No. XM_231705 *Rattus norvegicus* similar to enhancer of zeste homolog 2, (Drosophila) [*Mus musculus*] (LOC312299), mRNA, created Jan. 13, 2003.

NCBI Accession No. NM_007971 *Mus musculus* enhancer of zeste homolog 2 (Drosophila) (Ezh2), mRNA, created Jan. 4, 2000.

NCBI Accession No. BC015704 *Homo sapiens* suppressor of zeste 12 homolog (Drosophila), mRNA (cDNA clone MBC:10177 Image:3908024), complete cds, created Oct. 11, 2001.

NCBI Accession No. U97675 *Mus musculus* embryonic ectoderm development protein (EED) mRNA, complete cds, created May 14, 1997.

NCBI Accession No. AF080227 *Homo sapiens* embryonic ectoderm development protein mRNA, complete cds, created Aug. 15, 1998.

NCBI Accession No. XM_214996 Predicted: *Rattus norvegicus* embryonic ectoderm development (predicted) (Eed_predicted), mRNA, created Jan. 13, 2003.

NCBI Accession No. BC015704 *Homo sapiens* suppressor of zeste 12 homolog (Drosophila), mRNA (cDNA clone MGC:10177 IMAG:3908024, complete cds, created Oct. 11, 2001.

Brown, J. Leslie et al., "The *Drosophila* Polycomb Group Gene *pleiohomeotic* Encodes a DNA Binding Protein with Homology to the Transcription Factor YY1," Molecular Cell, vol. 1, 1057-1064, Jun. 1998.

Francis, Nicole J et al., "Mechanisms of Transcriptional Memory", Nature Reviews, Molecular Cell Biology, vol. 2, pp. 409-421, Jun. 2001.

Levine, Stuart S. et al., "The Core of the Polycomb Repressive Complex Is Compositionally and Functionally Conserved in Files and Humans" Molecular and Cell Biology, vol. 22, No. 17, p. 6070-6078, Sep. 2002.

Otto, Aric P. et al, "Gene repression by Polycomb group protein complexes: a distinct complex for every occasion?", Current in Genetics & Development 2003, 13:448-454.

Poux, Sylvain et al., "Establishing of Polycomb silencing requires a transient interaction between PC and ESC", Genes & Development 15:2509-2514, 2001.

Satijn, David P.E. et al., "RING1 Interacts with Multiple Polycomb-Group Proteins and Displays Tumorigenic Activity", Molecular and Cell Biology, vol. 19, No. 1, Jan. 1999, p. 57-68.

Satijn David P. E. et al., "The Polycomb Group Protein EED Interacts with YYI, and Both Proteins Induce Neural Tissue in *Xenopus* Embryos", Molecular and Cell Biology, vol. 21, No. 4, Feb. 2001, p. 1360-1369.

Tie, Feng et al, "A 1-Megadalton ESC/E(Z) Complex from *Drosophila* That Contains Polycomblike and RPD3", Molecular and Cell Biology, vol. 23, No. 9, May 2003, p. 3352-3362.

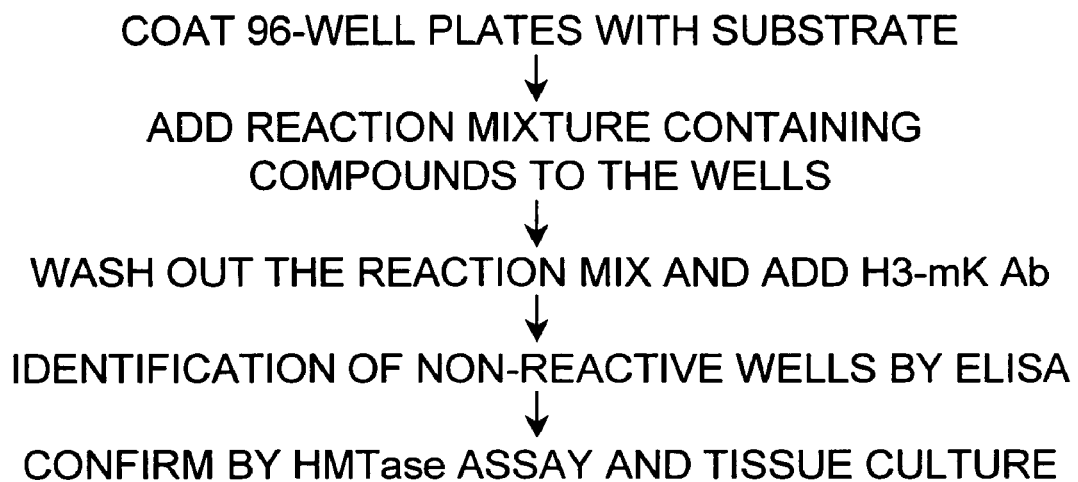
FIG. 7
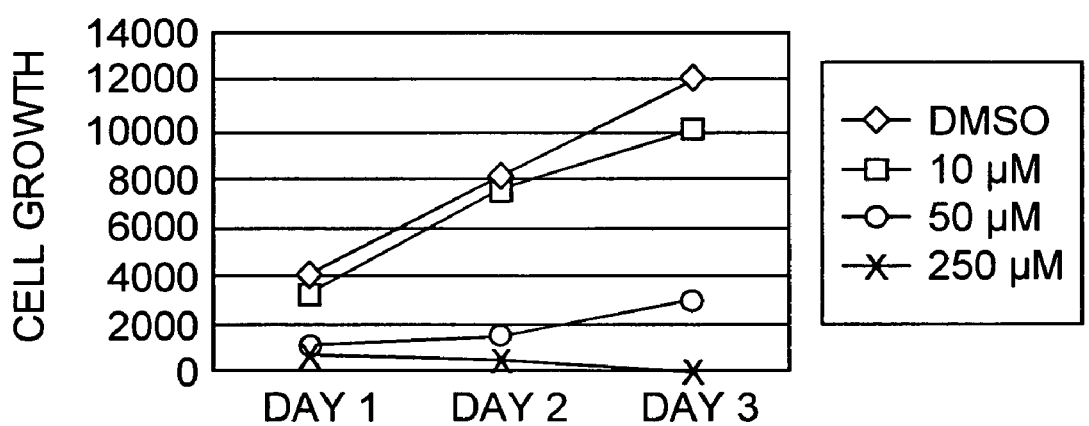

RECONSTITUTED HISTONE METHYLTRANSFERASE COMPLEX AND METHODS OF IDENTIFYING MODULATORS THEREOF

RELATED APPLICATION INFORMATION

This application claims the benefit of priority from U.S. Provisional Patent Application Ser. No. 60/575,880, filed Jun. 1, 2004, which is incorporated herein by reference in its entirety.

GOVERNMENT INTEREST

This invention was made, in part, with government support under grant numbers GM68804 and 5-R01-GM63067-01 from the National Institutes of Health. The U.S. Government has certain rights in the invention.

FIELD OF THE INVENTION

The present invention relates to a reconstituted histone methyltransferase complex and methods of identifying modulators thereof.

BACKGROUND OF THE INVENTION

Polycomb group (PcG) and trithorax group (trxG) proteins are known to be part of the cellular memory system (Francis and Kingston (2001) *Nat. Rev. Mol. Cell Biol.* 2:409-421; Simon and Tamkun (2002) *Curr. Opin. Genet. Dev.* 12:210-218). Both groups of proteins are involved in maintaining the spatial patterns of homeotic box (Hox) gene expression, which are established early in embryonic development by transiently expressed segmentation genes. In general, PcG proteins are transcriptional repressors that maintain the "off state," and trxG proteins are transcriptional activators that maintain the "on state." As members of PcG and trxG proteins contain intrinsic histone methyltransferase (HMTase) activity, PcG and trxG proteins may participate in cellular memory through methylation of core histones (Beisel, et al. (2002) *Nature* 419:857-862; Cao, et al. (2002) *Science* 298:1039-1043; Czermin, et al. (2002) *Cell* 111:185-196; Kuzmichev, et al. (2002) *Genes Dev.* 16:2893-2905; Milne, et al. (2002) *Mol. Cell* 10:1107-1117; Muller, et al. (2002) *Cell* 111:197-208; Nakamura, et al. (2002) *Mol. Cell* 10:1119-1128).

Biochemical and genetic studies have provided evidence that *Drosophila* PcG proteins function in at least two distinct protein complexes, the Polycomb repressive complex 1 (PRC1) and the ESC-E(Z) complex, although the compositions of the complexes may be dynamic (Otte and Kwaks (2003) *Curr. Opin. Genet. Dev.* 13:448-454). Studies in *Drosophila* (Czermin, et al. (2002) *Cell* 111:185-196; Muller, et al. (2002) *Cell* 111:197-208) and mammalian cells (Cao, et al. (2002) *Science* 298:1039-1043; Kuzmichev, et al. (2002) *Genes Dev.* 16:2893-2905) have demonstrated that the ESC-E(Z)/EED-EZH2 complexes have intrinsic histone methyltransferase activity. Although the compositions of the complexes isolated by different groups are slightly different, they generally contain EED, EZH2, SUZ12, and RbAp48 or *Drosophila* homologs thereof.

In addition to Hox gene silencing, EED-EZH2-mediated histone H3-K27 methylation has been shown to participate in X-inactivation (Plath, et al. (2003) *Science* 300:131-135; Silva, et al. (2003) *Dev. Cell* 4:481495). Recruitment of the EED-EZH2 complex to Xi and subsequent trimethylation on histone H3-K27 occurs during the initiation stage of X-inactivation and is dependent on Xist RNA. Furthermore, EZH2 and its associated histone H3-K27 methyltransferase activity was found to differentially mark the pluripotent epiblast cells and the differentiated trophectoderm (Erhardt, et al. (2003) *Development* 130:4235-4248). Consistent with a role of EZH2 in maintaining the epigenetic modification patterns of pluripotent epiblast cells, Cre-mediated deletion of EZH2 results in loss of histone H3-K27 methylation in these cells (Erhardt, et al. (2003) *Development* 130:4235-4248). Further, studies in prostate and breast cancer cell lines and tissues have revealed a strong correlation between the levels of EZH2 and SUZ12 and the invasiveness of these cancers (Bracken, et al. (2003) *EMBO J.* 22:5323-5335; Kirmizis, et al. (2003) *Mol. Cancer Ther.* 2:113-121; Kleer, et al. (2003) *Proc. Natl. Acad. Sci. USA* 100:11606-11611; Varambally, et al. (2002) *Nature* 419: 624-9), indicating that dysfunction of the EED-EZH2 complex may contribute to cancer.

Given that the EED-EZH2 complex-mediated histone H3-K27 methylation participates in a variety of important processes, there is a need in the art for agents that modulate the activity of this complex and methods for identifying the same.

SUMMARY OF THE INVENTION

The present invention reveals the intrinsic histone methyltransferase (HMTase) activity of a reconstituted complex comprising EZH2, EED and SUZ12, with or without RbAp48 and/or AEBP2, wherein the reconstituted complex facilitates homeotic box (Hox) gene silencing, participates in X-inactivation, plays a role in germline development and/or plays a role in stem cell pluripotency. The native complex has also been associated with cancer. Accordingly, the methods of the invention can be practiced to identify compounds to treat cancer and/or compounds that modulate Hox gene silencing, X-inactivation, genomic imprinting, stem cell pluripotency and/or germline development.

The mechanism by which histone methylation participates in transcriptional regulation is best illustrated by the HMTase SUV39H1 and its functional partner HP1. A model is suggested wherein SUV39H1, and its *S. pombe* homolog Clr4, methylate lysine 9 of histone H3 thereby creating a binding site for subsequent recruitment of HP1 through its chromo domain (Bannister, et al. (2001) *Nature* 410:120-124; Lachner, et al. (2001) *Nature* 410:116-120; Lachner, et al. (2001) *Nature* 410:116-120; Nakayama, et al. (2001) *Science* 292: 110-113; Rea, et al. (2000) *Nature* 406:593-599). Similarly, the inventors have proposed that histone H3-K27 methylation by the ESC-E(Z)/EED-EZH2 complexes helps recruit the PRC1 complex through specific recognition of the methylated lysine 27 of histone H3 by the chromo domain of the Polycomb (Pc) protein (Cao and Zhang (2004) *Curr. Opin. Genet. Dev.* 14:155-164), a core component of the PRC1 complex (Francis, et al. (2001) *Mol. Cell* 8:545-556). Four lines of evidence are consistent with this suggestion. First, in vitro studies demonstrated that the Pc chromo domain has higher affinity toward lysine 27 methylated histone peptide when compared with its non-methylated counterpart (Cao, et al. (2002) *Science* 298:1039-1043; Czermin, et al. (2002) *Cell* 111:185-196; Kuzmichev, et al. (2002) *Genes Dev.* 16:2893-29). Second, chromatin immunoprecipitation (ChIP), coupled with RNAi experiments, have demonstrated that loss of ESC-E(Z) binding on the Polycomb responsive element (PRE) of the Ubx gene correlates with loss of histone H3-K27 methylation and concomitant loss of Pc binding (Cao, et al. (2002) *Science* 298:1039-1043). Third, structural studies have revealed that the amino acids of histone H3 preceding lysine 27 contribute to the specific recognition of the methylated lysine 27 by Pc chromo domain (Fischle, et al. (2003) *Genes Dev.* 17:1870-1881; Min, et al. (2003) *Genes Dev.* 17:1823-1828). Further, amino acid substitutions that abolish E(Z) HMTase activity also eliminate its ability to contribute to PcG silencing of the Ubx gene in wing imaginal discs (Muller, et al. (2002) *Cell* 111:197-20). Collectively, these data indicate that the HMTase activity of E(Z) plays an important role in recruiting the PRC1 complex as well as in Hox gene silencing.

Embodiments of the present invention provide a reconstituted complex comprising EED, EZH2 and SUZ12 wherein the reconstituted complex has histone methyltransferase (HMTase) activity for lysine 27 of histone H3 (H3-K27). In representative embodiments, the reconstituted complex further comprises RbAp48, AEBP2 or both. In still other embodiments, the reconstituted complex consists essentially of EED, EZH2 and SUZ12, wherein the reconstituted complex has histone methyltransferase (HMTase) activity for lysine 27 of histone H3 (H3-K27).

The present invention further provides methods of producing a reconstituted complex comprising providing a host cell comprising (a) a heterologous nucleic acid sequence encoding an EED protein; (b) a heterologous nucleic acid sequence encoding an EZH2 protein; and (c) a heterologous nucleic acid sequence encoding an SUZ12 protein, and culturing the host cell under conditions sufficient for expression of the proteins and production of the reconstituted complex.

In other embodiments, the present invention provides a host cell comprising (a) a heterologous nucleic acid sequence encoding an EED protein; (b) a heterologous nucleic acid sequence encoding an EZH2 protein; and (c) a heterologous nucleic acid sequence encoding an SUZ12 protein. In representative embodiments, the host cell is an insect cell. In still other embodiments, the insect cell is an Sf9 cell.

The present invention further provides methods of identifying a compound that modulates the histone methyltransferase (HMTase) activity for lysine 27 of histone H3 (H3-K27) of a reconstituted complex comprising EED, EZH2, and SUZ12, the method comprising contacting the reconstituted complex with a histone substrate in the presence of a test compound, and detecting the level of H3-K27 methylation under conditions sufficient to provide H3-K27 methylation, wherein a change in H3-K27 methylation as compared with the level of H3-K27 methylation in the absence of the test compound indicates that the test compound is a modulator of the H3-K27 HTMase activity of the reconstituted complex. In some embodiments, the identified compound is an inhibitor of HTMase activity. In other embodiments, the identified compound is an activator of HTMase activity.

In still other embodiments, the present invention provides methods of identifying a candidate compound for treating cancer comprising contacting a reconstituted complex comprising EED, EZH2 and SUZ12 with a histone substrate in the presence of a test compound, and detecting the level of histone methylation of lysine 27 of histone H3 (H3-K27) under conditions sufficient to provide H3-K27 methylation, wherein a reduction in H3-K27 methylation as compared with the level of H3-K27 methylation in the absence of the test compound indicates that the test compound is a candidate compound for the treatment of cancer.

The present invention further provides methods of inhibiting methylation of lysine 27 of histone H3 (H3-K27), comprising contacting a cell with an inhibitor of the H3-K27 histone methyltransferase (HMTase) activity of a reconstituted complex comprising EED, EZH2 and SUZ12. In representative embodiments, the cell is a cultured cell. In other representative embodiments, the cell is a cell in vivo in a subject.

Embodiments of the present invention further provide reagents for increasing sensitivity of detection of methylation of lysine 27 of histone H3 (H3-K27), comprising a reconstituted complex comprising EED, EZH2 and SUZ12, optionally in a suspension medium.

The present invention further provides methods of identifying a compound that derepresses Hox gene (e.g., HoxA9) expression comprising contacting a reconstituted complex comprising EED, EZH2 and SUZ12 with a histone substrate in the presence of a test compound, and detecting the level of histone methylation of lysine 27 of histone H3 (H3-K27) under conditions sufficient to provide H3-K27 methylation, wherein a reduction in H3-K27 methylation as compared with the level of H3-K27 methylation in the absence of the test compound indicates that the test compound is a candidate compound for Hox gene derepression.

These and other aspects of the invention are set forth in more detail in the detailed description below.

BRIEF DESCRIPTION OF THE DRAWINGS

FIG. 1A depicts a schematic representation of the steps involved in EED-EZH2 reconstitution. FIG. 1B shows a silver-stained polyacrylamide-SDS gel (top panel), and HMTase activity assay (second panel) of the fractions derived from the SUPEROSE® 6 gel-filtration column. The five components of the recombinant EED-EZH2 complex are indicated by "*". The arrowhead indicates an EZH2 degradation product confirmed by western blot analysis (third panel). The elution profile of the protein markers is indicated at the top. The positions of the protein size markers are indicated on the left. The migration of recombinant AEBP2 (35-kDa), confirmed by western blot analysis (fourth panel), is different from that when it is in the native complex (65-kDa). FIG. 1C shows a comparison of the HMTase activity (bottom panel) of native complex (lane 1) with varying amounts of reconstituted complex (lanes 3-5) (top two panels) when equal amounts of nucleosomal histone are used (third panel). The amount of complex used was quantified by western blot analysis of EZH2 and SUZ12 as indicated. FIG. 1D is a characterization of the substrate specificity of the recombinant EED-EZH2 complex. Equal amounts of the recombinant enzyme complex were used to methylate equal amounts of histone H3 alone or in octamer, mono-, and oligonucleosome forms (bottom panel). The top panel is an autoradiograph of the bottom panel. Quantification of the top panel is presented in the middle panel with error bars from two independent experiments.

FIG. 2A shows GST pull-down assays using equal amounts of GST-fusion proteins (top panel) and in vitro translated, $S^{35}$-labeled proteins indicated on right (bottom panels). "In" represents 10% of the total Input. FIG. 2B is a schematic representation of the interactions detected in FIG. 2A. FIG. 2C shows mapping of the regions on AEBP2 involved in SUZ12 and RbAp48 interaction. Different deletion constructs (top panel) were in vitro transcribed/translated before being used in GST pull-down assays (bottom panels). The three zinc fingers on AEBP2 are indicated. The strength of the interaction is summarized on the right of the top panel. "++", "+", and "−" represent strong, weak, and no interaction, respectively.

FIG. 3A is a silver-stained polyacrylamide-SDS gel containing the purified recombinant complex and sub-complexes. (EED-EZH2)$_5$ contains all five components; (EED-EZH2)$_4$ does not contain AEBP2; (EED-EZH2)$_3$ does not contain AEBP2 and RbAp48; (EED-EZH2)$_2$ only have EED and EZH2. The different forms of FLAG®-EED were verified by western blot analysis. FIG. 3B shows a comparison of the enzymatic activity of the different recombinant complexes with 5, 4, 3, and 2 components. The complexes used were normalized so that each reaction contains equal amounts of EZH2 and chicken oligonucleosomes (top two panels). Reactions were performed with an enzyme/substrate ratio of 1:20. The enzymatic activity (third panel) and quantification (bottom panel) with error bars from two independent experiments are shown. FIG. 3C shows a comparison of the enzymatic activity of the different recombinant complexes with a wide range of enzyme concentrations indicated at the top of the panels. The oligonucleosome substrate used in each reaction was about 200 nM. Quantification of the data on top panels is presented in the bottom panel.

FIG. 4A shows that the EED-EZH2 complex, with or without AEBP2, has the same substrate preference. Equal amounts of the four-component recombinant enzyme complex were used to methylate equal amounts of histone H3 alone or in octamer, mono-, and oligonucleosome forms (bottom panel). The top panel is an autoradiograph of the bottom panel. Quantification of the top panel is presented in the middle panel with error bars from two independent experiments. FIG. 4B shows that histone H3-K27 is the target site for the reconstituted enzyme complexes with 5, 4, and 3 components. Three levels (indicate on top of the panels) of wild-type or mutant histone H3 were methylated with different reconstituted complexes with an enzyme/substrate ratio of 1:20. The activities were shown by autoradiography (first three columns).

FIG. 5A shows western blot (left panel) and quantitative RT-PCR (right panel) analysis of a SUZ12 stable knock-down cell line and a parallel mock knock-down cell line. Tubulin serves as a loading control for western blot analysis. GAPDH was used as control for normalization in the quantitative RT-PCR. FIG. 5B depicts the morphological change and cell growth inhibition in SUZ12 knock-down cells. Top panels show morphological changes of control and knock-down HeLa cells after 2 weeks of selection. Bottom panel shows the growth curve of control and knock-down HeLa cells. Viable cells were counted by trypan blue staining at different times after initial seeding of 4×10$^4$ cells. FIG. 5C shows western blot analysis of histones extracted from control and knock-down HeLa cells with antibodies specific for mono-, di- or tri-methylated K27 and trimethylated K9. Equal loading of histone H3 was verified by COOMASSIE® staining of a parallel gel (bottom panel).

FIG. 6A shows quantitative RT-PCR analysis of HoxC6, HoxC8, and HoxA9 expression in SUZ12 knock-down and mock knock-down cells. GAPDH was used as a control for normalization. Quantification is an average of two independent experiments with error bars. FIG. 6B shows chromatin immunoprecipitation (ChIP) analysis of selected regions covering the HoxA9 gene. Top panel is a diagram of the HoxA9 gene where the two exons are indicated by the two boxes. The locations of the analyzed regions (A to D) relative to the transcription start site are indicated. Each region covers about 500 bp. Three antibodies (anti-2mK4, -3mK27, and -SUZ12) and an IgG control were used in the ChIP assays using SUZ12 or mock knock-down cells. ChIP results were revealed by ethidium bromide staining of agarose gels containing PCR-amplified ChIP DNA.

FIG. 7 demonstrates the use of a reconstituted EED-EZH2 enzyme complex for identifying inhibitors in a high throughput screening assay. Specifically, FIG. 7 depicts a schematic representation of the steps involved in a high throughput assay for EED-EZH2 complex inhibitors.

DETAILED DESCRIPTION

Figure 1A:
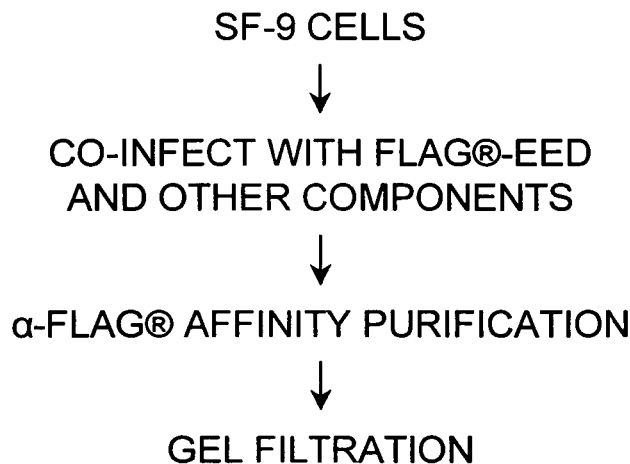
FIGS. 1A through 1D demonstrate that reconstituted EED-EZH2 complex has similar enzymatic activity and substrate specificity as that of the native complex.

The present invention will now be described in more detail with reference to the accompanying drawings, in which embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

As used in the description of the invention and the appended claims, the singular forms "a," "an" and "the" are intended to include the plural forms as well, unless the context clearly indicates otherwise. Also, as used herein, "and/or" refers to and encompasses any and all possible combinations of one or more of the associated listed items, as well as the lack of combinations when interpreted in the alternative ("or"). The term "about," as used herein when referring to a measurable value such as an amount of protein, dose, time, temperature, enzymatic activity or other biological activity and the like, is meant to encompass variations of 20%, 10%, 5%, 1%, 0.5%, or even 0.1% of the specified amount.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning" A Laboratory Manual 2nd Ed. (Cold Spring Harbor, N.Y., 1989); F. M. Ausubel et al. Current Protocols in Molecular Biology (Green Publishing Associates, Inc. and John Wiley & Sons, Inc., New York).

Chromatin structure plays a role in gene regulation and epigenetic inheritance. Post-translational modifications of histones are involved in the establishment and maintenance of higher-order chromatin structure. Further, it has been reported that the tails of certain core histones can be modified by acetylation, methylation, phosphorylation, ribosylation and ubiquitination. The present invention is based, in part, on the reconstitution of a protein complex that exhibits methyltransferase (HMTase) activity.

I. Reconstituted Protein Complex

According to some embodiments, the present invention provides a reconstituted complex comprising, consisting essentially of or consisting of EED, EZH2 and SUZ12 wherein the reconstituted complex has histone methyltransferase (HMTase) activity for lysine residues of histone H3. In particular embodiments, the reconstituted complex has HMTase activity for lysine 27 of histone H3 (H3-K27). In some embodiments, the reconstituted complex comprising EED, EZH2 and SUZ12 further comprises RbAp48, AEBP2 or both. Accordingly, the reconstituted complex can comprise EED, EZH2 and SUZ12, with or without RbAp48 and/or AEBP2. In particular embodiments, the complex does not comprise RbAp48.

In representative embodiments, the reconstituted complex has HMTase activity that is specific for H3-K27, meaning that substantially all of the observed HMTase activity is directed to H3-K27 (e.g., at least about 75%, 80%, 85%, 90%, 95%, 98% or more). In some embodiments of the invention, there is no, or essentially no, detectable methylation at sites other than H3-K27. In still other embodiments, some methylation (e.g., less than 5% or 10%) is detected at other sites, e.g., H3-K9.

As used herein, "reconstituted" refers to a recombinant complex that is formulated from individual, isolated components. As used herein, "recombinant" refers to a product formed by using recombinant technology, i.e., created utilizing genetic engineering techniques, which are well known in the art.

As used herein, "isolated" refers to a component that is separated or substantially free from at least some of the other components or associated elements of the naturally occurring complex to which the component is associated.

The terms "EED", "EZH2", "SUZ12", "RbAp48" and/or "AEBP2" as described herein encompass homologs from various organisms. In particular embodiments, EED, EZH2, SUZ12, RbAp48 and/or AEBP2 can be mammalian (e.g., human, simian, rat, mouse, feline, canine, bovine, equine, ovine, caprine, lagomorph, etc.) proteins, *Drosophila* proteins (e.g., ESC, E(Z), Su(z)12 and p55) nematode proteins (e.g., MES-2, MES-3 and MES-4), plant proteins or combinations thereof. A "combination thereof" of the proteins described above indicates that at least one protein can be derived from one organism and at least one protein can be derived from a different organism. For example, EED can be a mammalian protein and EZH2 can be a plant protein.

It will be further understood that the terms EED, EZH2, SUZ12, RbAp48 and/or AEBP2 can encompass a functional or biologically active variant, isoform, derivative, fragment or the like thereof as understood by those skilled in the art. As used herein, "variant" refers to an amino acid sequence that is altered by one or more amino acids. The variant may have "conservative" changes, wherein a substituted amino acid has similar structural or chemical properties. In particular, such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Iie, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function.

Alternatively, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE™ software. In particular embodiments, a "functional variant" retains at least one biological activity normally associated with the component of interest (e.g., H3-K27 HMTase activity). In particular embodiments, the "functional variant" retains at least about 40%, 50%, 60%, 75%, 85%, 90%, 95% or more biological activity normally associated with the natural component (e.g., K27 specific HMTase activity).

As used herein, "derivative" refers a component that has been subjected to a chemical modification. Derivatization of a protein component can involve the replacement of a hydrogen by an acetyl, acyl, alkyl, amino, formyl, or morpholino group. Derivative molecules can retain the biological activities of the naturally occurring molecules but can confer advantages such as longer lifespan or enhanced activity.

In particular embodiments, a biologically active variant or derivative of any of the protein components of the reconstituted complex has at least about 60%, 70%, 75%, 80%, 85%, 90%, 95% 98% or more amino acid sequence similarity or identity with the amino acid sequence of a naturally-occurring protein.

As used herein, "fragment" refers to a portion of the component that retains at least one biological activity normally associated with that component (e.g., H3-K27 HMTase activity) and can have at least about 50%, 70%, 80%, 90% or more of the biological activity as compared with the full-length protein or even has a greater level of biological activity. For example, in particular embodiments, a fragment of EZH2 comprises the catalytic domain, the SAM binding site and/or the SET domain. Generally, the fragment retains the ability to participate in complex formation. In representative embodiments, the fragment comprises at least about 50, 100, 150, 200, 250 or 500 consecutive amino acids of the full-length protein.

Isoforms of the components of the reconstituted complex are well known in the art. For example, Kuzmichev, et al. *Mol. Cell* 14(2):183-93 (2004) and Pasini et al. *Cell Cycle* 3: 22-26 (2004) describe EED isoforms. See also, e.g., GenBank Accession Nos. NM_004456 and NP_004447 (EZH2, human isoform a); GenBank Accession Nos. NM_152998 and NP_694543 (EZH2, human isoform b); GenBank Accession Nos. NM_003797 and NP_003788 (EED, human isoform a); GenBank Accession Nos. NM_152991 and NP_694536 (EED, human isoform b); GenBank Accession Nos. NM_143802 and NP_652059 (SU(Z)12, isoform a from *Drosophila melanogaster*); and GenBank Accession Nos. NM_168826 and NP_730465 (SU(Z)12, isoform b from *Drosophila melanogaster*).

In further embodiments, the reconstituted complex of the present invention has enzyme activity comparable to the enzyme activity of a native complex (e.g., at least 70%, 80%, 90%, 95% or more). In other embodiments, the reconstituted complex has substrate specificity comparable to the substrate specificity of a native complex (e.g., preference for H3 in nucleosome form and further a preference for H3 in dinucleosome or oligonucleosome as compared with mononucleosome form). In particular embodiments, the histone substrate is a core histone or histone complex (i.e., free or essentially free of DNA). In some embodiments, the histone substrate is present in a nucleosome (i.e., the reconstituted complex is contacted with a nucleosome comprising the histone substrate). More particularly, the histone substrate can be a core histone, a histone octamer or a nucleosome including, but not limited to, a mononucleosome, a dinucleosome or an oligonucleosome. In particular embodiments, the histone substrate is a dinucleosome.

The present invention further provides a method of producing the reconstituted complex of the present invention, the method comprising, consisting essentially of or consisting of providing a host cell comprising heterologous nucleic acid sequences encoding proteins of the reconstituted complex and culturing the host cell under conditions sufficient for expression of the proteins and production of the reconstituted complex. In particular embodiments, in the method of producing the reconstituted complex, the host cell comprises (a) a heterologous nucleic acid sequence encoding an EED protein; (b) a heterologous nucleic acid sequence encoding an EZH2 protein; and (c) a heterologous nucleic acid sequence encoding a SUZ12 protein, and culturing the host cell under conditions sufficient for expression of the proteins and production of the reconstituted complex. In some embodiments, the host cell further comprises (d) a nucleic acid sequence encoding an RbAp48 protein, (e) a nucleic acid sequence encoding an AEBP2 protein, or (f) both.

As used herein, "nucleic acid" encompasses both RNA and DNA, including cDNA, genomic DNA, synthetic (e.g., chemically synthesized) DNA and chimeras of RNA and DNA. The nucleic acid may be double-stranded or single-stranded. Where single-stranded, the nucleic acid may be a sense strand or an antisense strand. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

The term "heterologous nucleic acid" is a well-known term of art and would be readily understood by one of skill in the art to be a nucleic acid that is not normally present within the host cell into which it has been introduced and/or is a nucleic acid that is expressed under the control of regulatory elements that are not normally present within the host cell. A heterologous nucleic acid of this invention can also be a nucleic acid that is present in an amount, or expressed in an amount, that is not normally the amount present in the cell into which the nucleic acid has been introduced. The heterologous nucleic acid will typically be a sequence that is not naturally occurring in the host cell. Additionally, the heterologous nucleic acids encoding the components of the reconstituted complex can be associated with appropriate expression control sequences, e.g., transcription/translation control signals and polyadenylation signals.

It will be appreciated that a variety of promoter/enhancer elements can be used depending on the level and tissue-specific expression desired. The promoter can be constitutive or inducible (e.g., the metalothionein promoter or a hormone inducible promoter), depending on the pattern of expression desired. The promoter can be native or foreign and can be a natural or a synthetic sequence. By foreign, it is intended that the promoter is not found in the wild-type host into which the promoter is introduced. The promoter is chosen so that it will function in the target cell(s) of interest. Moreover, specific initiation signals are generally required for efficient translation of inserted protein coding sequences. These translational control sequences, which can include the ATG initiation codon and adjacent sequences, can be of a variety of origins, both natural and synthetic. In embodiments of the invention wherein the heterologous nucleic acids encoding the components of the reconstituted complex comprise an additional sequence to be transcribed, the transcriptional units can be operatively associated with separate promoters or with a single upstream promoter and one or more downstream internal ribosome entry site (IRES) sequences (e.g., the picornavirus EMC IRES sequence).

Suitable host cells are well known in the art. See e.g., Goeddel, *Gene Expression Technology*: Methods in Enzymology 185, Academic Press, San Diego, Calif. (1990). For example, the host cell can be a prokaryotic or eukaryotic cell. Further, it is well known that polypeptides and/or proteins can be expressed in bacterial cells such as *E. coli*, insect cells (e.g., the baculovirus expression system), yeast cells, plant cells or mammalian cells (e.g. human, rat, mouse, bovine, porcine, ovine, caprine, equine, feline, canine, lagomorph, simian and the like). The host cell can be a cultured cell such as a cell of a primary or immortalized cell line. The host cell can be a cell in a microorganism, animal or plant being used essentially as a bioreactor. In particular embodiments of the present invention, the host cell is any insect cell that allows for replication of well-known expression vectors. For example, the host cell can be from *Spodoptera frugiperda*, such as the Sf9 or Sf21 cell lines, *drosophila* cell lines, or mosquito cell lines, e.g., *Aedes albopictus* derived cell lines. Use of insect cells for expression of heterologous proteins is well documented, as are methods of introducing nucleic acids, such as vectors, e.g., insect-cell compatible vectors, into such cells and methods of maintaining such cells in culture. See, for example, Methods in Molecular Biology, ed. Richard, Humana Press, NJ (1995); O'Reilly et al., Baculovirus Expression Vectors, A Laboratory Manual, Oxford Univ. Press (1994); Samulski et al., J. Vir. 63:3822-8 (1989); Kajigaya et al., Proc. Nat'l. Acad. Sci. USA 88: 4646-50 (1991); Ruffing et al., J. Vir. 66:6922-30 (1992); Kimbauer et al., Vir. 219:37-44 (1996); Zhao et al., Vir. 272:382-93 (2000); and Samulski et al., U.S. Pat. No. 6,204,059. In particular embodiments of the present invention, the insect cell is an Sf9 cell.

In some embodiments, the method of producing the reconstituted complex further comprises isolating the expressed reconstituted complex from the cultured host cell or a culture medium from the cultured host cell. The isolated reconstituted complex can be isolated and purified according to well-known protein isolation and purification techniques that can involve a combination of procedures and iterations of the same in an effort to obtain the desired amount of protein and level of purity.

Accordingly, in some embodiments, the method of producing the reconstituted complex comprises binding the expressed reconstituted complex to a solid support. The solid support can be an inorganic and/or organic particulate support material comprising sand, silicas, silicates, silica gel, glass, glass beads, glass fibers, alumina, zirconia, titania, nickel, and suitable polymer materials including, but are not limited to, agarose, polystyrene, polyethylene, polyethylene glycol, polyethylene glycol grafted or covalently bonded to polystyrene (also termed PEG-polystyrene), in any suitable form known to those of skill in the art such as a particle, bead, gel or plate. The solid support can comprise a moiety, as known to those skilled in the art, that can be used to bind to the expressed reconstituted complex, e.g., nickel, an antibody or an enzyme substrate (e.g. glutathione) directed to the expressed reconstituted complex. Detection can be facilitated by coupling or tagging (i.e., physically linking) the desired protein or antibody directed to the protein to an appropriate detectable substance, including commercially available detectable substances. Examples of detectable substances include, but are not limited to, various antibodies, enzymes, peptide and/or protein tags, prosthetic groups, fluorescent materials, luminescent materials, bioluminescent materials, and radioactive materials. Examples of suitable antibodies, for example antibodies against EZH2 and SUZ12, have been described in Cao et al. *Science* 298: 1039-1043 (2002), Peters et al. *Mol. Cell* 12: 1577-1589 (2003); and Plath et al. *Science* 300: 131-135 (2003). Examples of suitable enzymes include, but are not limited to, glutathione S-transferase (GST), horseradish peroxidase, alkaline phosphatase, β-galactosidase, or acetylcholinesterase. Examples of peptide and/or protein tags include, but are not limited to, a polyhistidine peptide tag, the FLAG peptide tag, maltose binding protein (MBP), thioredoxin (Trx) and calmodulin binding peptide. Examples of suitable prosthetic group complexes include, but are not limited to, streptavidin/biotin and avidin/biotin. Examples of suitable fluorescent materials include, but are not limited to, umbelliferone, fluorescein, fluorescein isothiocyanate, rhodamine, dichlorotriazinylamine fluorescein, dansyl chloride or phycoerythrin. An example of a luminescent material includes luminal. Examples of bioluminescent materials include, but are not limited to, luciferase, luciferin, and aequorin. Examples of suitable radioactive material include, but are not limited to, $^{125}I$, $^{131}I$, $^{35}I$ and $^{3}H$. In particular embodiments, the expressed reconstituted complex comprises a purification tag (e.g., any one or more of the components can be tagged). In some embodiments, the reconstituted complex of the present invention has a purity level of at least about 40%, 50%, 60%, 70%, 80%, 90%, 95%, 97%, 98%, 99% or more (w/w).

In further embodiments of the present invention, the host cell can be stably transformed with the heterologous nucleic acid sequences encoding the proteins described above. "Stable transformation" as used herein generally refers to the integration of the heterologous nucleic acid sequences into the genome of the host cell in contrast to "transient transformation" wherein the heterologous nucleic acid sequences introduced into the host cell do not integrate into the genome of the host cell. The term "stable transformant" can further refer to stable expression of an episome (e.g. Epstein-Barr Virus (EBV)).

In particular embodiments, the host cell is stably transformed with the heterologous nucleic acid sequences encoding an EED protein, an EZH2 protein and a SUZ12 protein, and optionally an RbAp48 protein, an AEBP2 protein, or both.

In some embodiments, the host cell comprises one or more recombinant vectors comprising the heterologous nucleic acid sequences encoding the proteins described above, in particular, an EED protein, an EZH2 protein and a SUZ12 protein. As used herein, "recombinant vector" refers to a viral or non-viral vector that comprises one or more heterologous nucleotide sequences (i.e., transgenes), e.g., two, three, four, five or more heterologous nucleotide sequences. In particular embodiments, the one or more vectors comprise (i) a vector comprising a heterologous nucleic acid sequence encoding an EED protein, (ii) a separate vector comprising a heterologous nucleic acid sequence encoding an EZH2 protein, and (iii) a further separate vector comprising a heterologous nucleic acid sequence encoding a SUZ12 protein. In other embodiments, methods of producing the reconstituted complex further comprise transforming the host cell with the one or more vectors. The components of the reconstituted complex can each be expressed from a separate vector. Alternatively, a single vector can encode one or more of the components of the reconstituted complex.

Suitable vectors include virus vectors (e.g., baculovirus, retrovirus, alphavirus, vaccinia virus, adenovirus, adeno-associated virus, or herpes simplex virus), lipid vectors, polylysine vectors, synthetic polyamino polymer vectors that are used with nucleic acid molecules, such as plasmids, and the like. Delivery vectors are described in more detail in Section IV.

In further embodiments, the present invention provides a host cell comprising, consisting essentially of or consisting of heterologous nucleic acid sequences encoding each of the proteins of the reconstituted complex. In particular embodiments, the host cell comprises, consists essentially of or consists of (a) a heterologous nucleic acid sequence encoding an EED protein, (b) a heterologous nucleic acid sequence encoding an EZH2 protein, and (c) a heterologous nucleic acid sequence encoding a SUZ12 protein, and optionally a heterologous nucleic acid sequence encoding (d) an RbAp48 protein, (e) a nucleic acid sequence encoding an AEBP2 protein, or (f) both. Suitable host cells are described above. In some embodiments, the host cell is an insect cell. In particular embodiments, the insect cell is an Sf9 cell.

Further, the host cell can be stably transformed with the heterologous nucleic acid sequences encoding proteins of the reconstituted complex, e.g. a heterologous nucleic acid sequence encoding an EED protein, a heterologous nucleic acid sequence encoding an EZH2 protein, a heterologous nucleic acid sequence encoding a SUZ12 protein, and optionally a heterologous nucleic acid sequence encoding an RbAp48 protein, a nucleic acid sequence encoding an AEBP2 protein, or both. In some embodiments, the host cell comprises one or more recombinant vectors comprising the heterologous nucleic acid sequences as described above. In further embodiments, the one or more vectors comprise a vector comprising a heterologous nucleic acid sequence encoding (i) an EED protein, (ii) a separate vector comprising a heterologous nucleic acid sequence encoding an EZH2 protein, and (iii) a further separate vector comprising a heterologous nucleic acid sequence encoding a SUZ12 protein. Suitable vectors are described herein. According to embodiments of the present invention, the vector can be a baculovirus vector.

Nucleic acid and amino acid sequences of EZH2, EED, SUZ12, AEBP2 and RbAp48 are known in the art, see e.g., Chen et al., (1996) *Genomics* 15; 38 (1):30-7 (EZH2); Schumacher et al., (1998) *Genomics* 15; 54(1):79-88 (EED); Kuzmichev et al., (2004) *Mol. Cell* 14(2):183-93 (EED); Pasini et al. (2004) *Cell Cycle* 3: 22-26 (EED); Birve et al., (2001) *Development* 128: 3371-3379 (SUZ12); Qian et al., (1993) *Nature* 264: 648-652 (RbAp48); Cao et al. (2004) *Mol. Cell* 15:57-67 and Zhang et al., (1999) *Genes Dev* 13:1924-1935 (baculovirus expressing mammalian RbAp48); He et al., (1999) *J. Biol. Chem.* 21; 274(21):14678-84 (AEBP2); GenBank Accession Nos. NM_004456 and NP_004447 (EZH2, human isoform a); GenBank Accession Nos. NM_152998 and NP_694543 (EZH2, human isoform b); GenBank Accession Nos. NM_079297 and NP_524021 (E(Z), *Drosophila melanogaster*); GenBank Accession Nos.

NM_003797 and NP_003788 (EED, human isoform a); GenBank Accession Nos. NM_152991 and NP_694536 (EED, human isoform b); GenBank Accession Nos. NM_058083 and NP_477431 (ESC, *Drosophila melanogaster*); GenBank Accession Nos. NM_015355 and NP_056170 (SUZ12, human); GenBank Accession Nos. NM_143802 and NP_652059 (SU(Z)12, isoform a from *Drosophila melanogaster*); GenBank Accession Nos. NM_168826 and NP_730465 (SU(Z)12, isoform b from *Drosophila melanogaster*); GenBank Accession Nos. NM_005610 and NP_005601 (RbAp48, human); and GenBank Accession Nos. NM_153207 and NP_694939 (AEBP2, human).

II. Screening Methods

The present invention further provides methods of identifying compounds that modulate the histone methyl transferase (HMTase) activity of the reconstituted complex described herein or modulate binding of the reconstituted complex to histone H3 and/or nucleosomes. As used herein, "modulate," "modulates" or "modulation" refers to enhancement (e.g., an increase) or inhibition (e.g., a reduction) in the specified activity. The term "enhancement," "enhance," "enhances," or "enhancing" refers to an increase in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase). The term "inhibit" or "reduce" or grammatical variations thereof as used herein refers to a decrease or diminishment in the specified activity of at least about 10%, 25%, 35%, 40%, 50%, 60%, 75%, 80%, 90%, 95% or more. In particular embodiments, the inhibition or reduction results in little or essentially no detectible activity (at most, an insignificant amount, e.g., less than about 10% or even 5%).

In some embodiments, the present invention provides methods of identifying a compound that modulates the HMTase activity for lysine 27 of histone H3 (H3-K27) of a reconstituted complex comprising EED, EZH2, and SUZ12, the method comprising, consisting essentially of or consists of contacting the reconstituted complex with a histone substrate in the presence of a test compound, and detecting the level of H3-K27 methylation under conditions sufficient to provide H3-K27 methylation, wherein a change in H3-K27 methylation as compared with the level of H3-K27 methylation in the absence of the test compound indicates that the test compound is a modulator of the H3-K27 HTMase activity of the reconstituted complex. In some embodiments, the reconstituted complex further comprises RbAp48, AEBP2 or both, wherein RbAp48 and/or AEBP2 are mammalian proteins, *drosophila* proteins, nematode proteins, plant proteins or combinations thereof. In particular embodiments, a reduction in H3-K27 methylation as compared with the level of H3-K27 methylation in the absence of the test compound indicates that the test compound is an inhibitor of the H3-K27 HMTase activity of the reconstituted complex. "Inhibitor" as used herein refers to the ability of the test compound to reduce the specified activity as compared to the level of activity in the absence of the test compound. In some embodiments, the test compound decreases or diminishes HTMase activity by at least about 10%, 25%, 35%, 40%, 50%, 60%, 75%, 80%, 90%, 95% or more as compared to the level of HTMase activity in the absence of the test compound. In particular embodiments, there is little or essentially no detectible activity (at most, an insignificant amount, e.g., less than about 10% or even 5%). In other embodiments, an increase in H3-K27 methylation as compared with the level of H3-K27 methylation in the absence of the test compound indicates that the test compound is an activator of the H3-K27 HMTase activity of the reconstituted complex. "Activator" as used herein refers to the ability of the test compound to increase or prevent a reduction of the specified activity as compared to the level of activity in the absence of the test compound. In some embodiments, there is at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase in HTMase activity.

Modulation of the HMTase activity of the reconstituted complex can be determined by any method known in the art, for example by, the addition of, e.g., a radiolabeled methyl donor such as S-adenosyl-L-methionine (SAM), into the reaction mixture or by monitoring histone H3 lysine 27 methylation by ELISA using a labeled antibody (e.g., a fluorescently labeled antibody) which specifically recognizes the methylated form of histone H3 lysine 27 as described in Wang et al. *Science* 293:853-857 (2001). Inhibitors or activators identified in the first round of screening can be analyzed individually in an assay to determine the $IC_{50}$ and specificity using HMTase assays as disclosed herein. Compounds having a lower $IC_{50}$ and exhibiting specificity for the EED-EZH2 enzyme can be further analyzed in tissue culture to determine their in vivo effects on H3-K27 methylation, cell growth (e.g., by trypsinization and trypan-blue staining) and/or toxicity.

Test compounds which can be screened in accordance with the methods provided herein encompass numerous chemical classes including, but not limited to, synthetic or semi-synthetic chemicals, purified natural products, proteins, antibodies, peptides, peptide aptamers, nucleic acids, oligonucleotides, carbohydrates, lipids, or other small or large organic or inorganic molecules. Small molecules are desirable because such molecules are more readily absorbed after oral administration and have fewer potential antigenic determinants. Non-peptide agents or small molecule libraries are generally prepared by a synthetic approach, but recent advances in biosynthetic methods using enzymes may enable one to prepare chemical libraries that are otherwise difficult to synthesize chemically. Small molecule libraries can also be obtained from various commercial entities, for example, SPECS and BioSPEC B.V. (Rijswijk, the Netherlands), Chembridge Corporation (San Diego, Calif.), Comgenex USA Inc., (Princeton, N.J.), Maybridge Chemical Ltd. (Cornwall, UK), and Asinex (Moscow, Russia).

In certain embodiments, the methods of identifying a compound that modulates the HTMase activity of the reconstituted complex described are cell-based methods or cell-free methods. In other embodiments, the methods provide high throughput screening capabilities to identify modulators of the reconstituted complex. For example, a cell-based, high throughput screening assay for use in accordance with the methods disclosed herein includes that disclosed by Stockwell, et al. ((1999) *Chem. Bio.* 6:71-83), wherein biosynthetic processes such as DNA synthesis and post-translational processes are monitored in a miniaturized cell-based assay. To illustrate, a cell-based assay to identify inhibitors of endogenous HMTase activity can encompass the use of a reporter gene, such as luciferase, operably linked to an upstream region of a target gene, such as a Hox gene, known to be targeted by HMTase. Cells expressing the reporter construct can be exposed to the test compound and reporter gene expression can be monitored. To confirm that the inhibitor is specifically targeting the reconstituted complex, a secondary in vitro screen can be employed using reconstituted complex. Alternatively, components of the reconstituted complex can be expressed in a cell that lacks an endogenous complex and used to directly screen for modulators.

High throughput, cell-free methods for screening small molecule libraries for candidate protein-binding molecules are well-known in the art and can be employed to identify molecules that bind to at least one component of the reconstituted complex and modulate the HMTase activity or binding to histone. For example, nucleosomal histone substrates (e.g., dinucleosomal histones) purified from HeLa cells can be coated on a multi-well plate or other suitable surface and a reaction mix containing the reconstituted enzyme complex added to the substrate. Prior to, concurrent with, or subsequent to the addition of the reconstituted complex, a test compound can be added to the well or surface containing the substrate. The reaction mixture can be washed with a solution that substantially reflects physiological conditions to remove unbound or weakly bound test compounds. Alternatively, the test compound can be immobilized and a solution of reconstituted complex can be contacted with the column, filter or other surface. The ability of a test compound to modulate binding of a reconstituted complex to histone can be determined by labeling (e.g., radio-labeling or chemiluminescence) or competitive ELISA assays.

Library screening can be performed in any format that allows rapid preparation and processing of multiple reactions. Stock solutions of the test agents as well as assay components are prepared manually and all subsequent pipetting, diluting, mixing, washing, incubating, sample readout and data collecting is done using commercially available robotic pipetting equipment, automated work stations, and analytical instruments for detecting the signal generated by the assay, i.e., methylation of histone H3 lysine 27.

A variety of other reagents can be included in the screening assay of the instant invention. These include reagents like salts, neutral proteins, e.g., albumin, detergents, etc. which can be used to facilitate optimal protein-protein binding and/or HMTase activity and/or reduce non-specific or background interactions. Also, reagents that otherwise improve the efficiency of the assay, such as protease inhibitors, nuclease inhibitors, anti-microbial agents, and the like may be used. The mixture of components can be added in any order that provides for the requisite binding and/or HMTase activity.

The present invention also provides methods of identifying a candidate compound for treating hyperproliferative disorders such as tumors, cancers, and neoplastic disorders, as well as premalignant and non-neoplastic or non-malignant hyperproliferative disorders comprising, consisting essentially of or consisting of contacting a reconstituted complex comprising EED, EZH2 and SUZ12 with a histone substrate in the presence of a test compound, and detecting the level of histone methylation of lysine 27 of histone H3 (H3-K27) under conditions sufficient to provide H3-K27 methylation, wherein a reduction in H3-K27 methylation as compared with the level of H3-K27 methylation in the absence of the test compound indicates that the test compound is a candidate compound for the treatment of hyperproliferative disorders such as tumors, cancers, and neoplastic disorders, as well as premalignant and non-neoplastic or non-malignant hyperproliferative disorders.

In particular embodiments, the present invention provides methods of identifying a candidate compound for treating cancer. Exemplary cancers include malignant disorders such as breast cancers; osteosarcomas; angiosarcomas; fibrosarcomas and other sarcomas; leukemias; lymphomas; sinus tumors; ovarian, uretal, bladder, prostate and other genitourinary cancers; colon, esophageal and stomach cancers and other gastrointestinal cancers; lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas. By the terms "treating cancer" or "treatment of cancer," it is intended that the severity of the cancer is reduced or the cancer is at least partially eliminated.

In some embodiments, compounds that serve as test compounds can be derived from a screen for SET domain-containing proteins including, but not limited to, SET7 inhibitors. The SET domain is a conserved sequence motif that may be a signature motif present in protein methyltransferases where several of the proteins possessed methyltransferase activity, including histone methylation. See Zhang et al. Transcription regulation by histone methylation: interplay between different covalent modifications of the core histone tails. Genes & Development 15:2343-2360 (2001).

III. Additional Uses and Subjects

In addition to the screening methods described above, the reconstituted complex of the present invention can be used as a research reagent, e.g., to identify compounds for modulating HTMase activity for studies of histone function. For example, identification of compounds that increase H3-K27 HMTase activity can be used to study the function of modifications as regulators of H3-K27 HMTase activity.

According to other embodiments, the present invention further provides methods of inhibiting histone methylation. In particular, methods of inhibiting methylation of lysine 27 of histone H3 (H3-K27), comprising, consisting essentially of or consisting of contacting a cell with an inhibitor of the H3-K27 histone methyltransferase (HMTase) activity of a reconstituted complex comprising EED, EZH2 and SUZ12. The reconstituted complex can further comprise RbAp48, AEBP2 or both. In some embodiments, the cell is a cultured cell. In other embodiments, the cell is a cell in vivo in a subject.

Subjects for which implementation of the present invention is appropriate include, but are not limited to, avians and mammals, with mammals being preferred. The term "avian" as used herein includes, but is not limited to, chickens, ducks, geese, quail, turkeys and pheasants. In some embodiments, human subjects are preferred. Human subjects include subjects of both genders and at any stage of development (i.e., neonate, infant, juvenile, adolescent, adult). While some embodiments of the present invention are primarily concerned with implementation regarding human subjects, the invention can also be carried out on animal subjects, particularly mammalian subjects such as non-human primates, bovines, ovines, caprines, equines, felines, canines, lagomorphs, rats, mice, etc. The present invention is carried out on animals for veterinary purposes, and for drug screening and drug development purposes.

In further embodiments, the present invention provides pharmaceutical preparations comprising an inhibitor of the reconstituted complex described above and a pharmaceutically acceptable carrier. The present invention further provides the use of the inhibitor of the reconstituted complex described above or the screening assays described herein for the preparation of a medicament.

Embodiments of the present invention further provide a reagent for increasing sensitivity of detection of histone methylation, in particular, methylation of lysine 27 of histone H3 (H3-K27), comprising, consisting essentially of or consisting of a reconstituted complex comprising EED, EZH2 and SUZ12. The reagent can further comprise a suspension medium. The reconstituted complex can further comprise RbAp48, AEBP2 or both. In some embodiments, the reagent is lyophilized. In particular embodiments, the reagent is a diagnostic reagent for cancer.

In further embodiments, the present invention provides a kit for determining inhibition of histone methylation, the kit comprising, consisting essentially of, consisting of (a) a reconstituted complex comprising EED, EZH2 and SUZ12; and (b) written instructions for methods for determining inhibition of histone methylation comprising determining the inhibition of the histone methyltransferase (HTMase) activity of the reconstituted complex, and optionally additional reagents or apparatus for carrying out methods for determining inhibition of HTMase activity. The reconstituted complex can further comprise RbAp48, AEBP2 or both. In particular embodiments, the method is directed to determining inhibition of histone methylation of lysine 27 of histone H3 (H3-K27), the kit comprising, consisting essentially of, consisting of (a) a reconstituted complex comprising EED, EZH2 and SUZ12, and (b) written instructions for methods for determining inhibition of H3-K27 methylation comprising determining the inhibition of H3-K27 methyltransferase (HTMase) activity of the reconstituted complex, and optionally additional reagents or apparatus for carrying out methods for determining inhibition of HTMase activity. In some embodiments, the reconstituted complex can further comprise RbAp48, AEBP2 or both.

IV. Delivery Vectors

Any viral vector that is known in the art can be used in the present invention. Examples of such viral vectors include, but are not limited to vectors derived from: Adenoviridae; Baculoviridae; Birnaviridae; Bunyaviridae; Caliciviridae, Capillovirus group; Carlavirus group; Carmovirus virus group; Group Caulimovirus; Closterovirus Group; Commelina yellow mottle virus group; Comovirus virus group; Coronaviridae; PM2 phage group; Corcicoviridae; Group Cryptic virus; group Cryptovirus; Cucumovirus virus group Family ([PHgr]6 phage group; Cysioviridae; Group Carnation ringspot; Dianthovirus virus group; Group Broad bean wilt; Fabavirus virus group; Filoviridae; Flaviviridae; Furovirus group; Group Germinivirus; Group Giardiavirus; Hepadnaviridae; Herpesviridae; Hordeivirus virus group; Illarvirus virus group; Inoviridae; Iridoviridae; Leviviridae; Lipothrixviridae; Luteovirus group; Marafivirus virus group; Maize chlorotic dwarf virus group; Icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Pea enation mosaic virus group; Phycodnaviridae; Picornaviridae; Plasmaviridae; Prodoviridae; Polydnaviridae; Potexvirus group; Potyvirus; Poxyiridae; Reoviridae; Retroviridae; Rhabdoviridae; Group Rhizidiovirus; Siphoviridae; Sobemovirus group; SSV 1-Type Phages; Tectiviridae; Tenuivirus; Tetraviridae; Group Tobamovirus; Group Tobravirus; Togaviridae; Group Tombusvirus; Group Torovirus; Totiviridae; Group Tymovirus; and plant virus satellites.

Protocols for producing recombinant viral vectors and for using viral vectors for nucleic acid delivery can be found in *Current Protocols in Molecular Biology*, Ausubel, F. M. et al. (eds.) Greene Publishing Associates, (1989) and other standard laboratory manuals (e.g., Vectors for Gene Therapy. In: *Current Protocols in Human Genetics*. John Wiley and Sons, Inc.: 1997).

In certain embodiments of the present invention, the delivery vector is a baculovirus vector.

The term "baculovirus" as used herein is intended to encompass all baculoviruses. Baculoviruses are divided into three subfamilies, including non-occluded baculoviruses (NOVs), granulosis viruses (GVs) and nuclear polyhedrosis viruses (NPVs). Although certain GVs and NOVs have been carefully studied, NPVs are the most thoroughly characterized of the baculovirus subfamilies. Examples of NPVs include *Autographa californica* NPV, *Spodoptera exigua* NPV, *Heliothis armigera* NPV, *Helicoverpa zea* NPV, *Spodoptera frugiperda* NPV, *Trichoplusia ni* NPV, *Mamestra brassicae* NPV, *Lymantria dispar* NPV, *Spodoptera litturalis* NPV, *Syngrapha facifera* NPV, *Choristoneura fumiferana* NPV, *Anticarsia gemmatalis* NPV, and *Heliothis virescens* NPV.

Standard procedures for engineering baculoviruses having various foreign genetic elements are well known in the art. Procedures for introducing recombinant baculoviruses into insects or cells thereof are also well known. See, e.g., Pfeifer et al., 1997, Gene 188:183-190; and Clem et al., 1994, J Virol 68:6759-6762. Baculoviruses expressing mammalian RbAp48 are described in Cao et al. *Mol. Cell* 15:57-67 (2004) and Zhang et al. *Genes Dev* 13:1924-1935 (1999).

The term "adenovirus" as used herein is intended to encompass all adenoviruses, including the *Mastadenovirus* and *Aviadenovirus* genera. To date, at least forty-seven human serotypes of adenoviruses have been identified (see, e.g., FIELDS et al., VIROLOGY, volume 2, chapter 67 (3d ed., Lippincott-Raven Publishers). Preferably, the adenovirus is a serogroup C adenovirus, still more preferably the adenovirus is serotype 2 (Ad2) or serotype 5 (Ad5).

The various regions of the adenovirus genome have been mapped and are understood by those skilled in the art (see, e.g., FIELDS et al., VIROLOGY, volume 2, chapters 67 and 68 (3d ed., Lippincott-Raven Publishers). The genomic sequences of the various Ad serotypes, as well as the nucleotide sequence of the particular coding regions of the Ad genome, are known in the art and can be accessed, e.g., from GenBank and NCBI (see, e.g., GenBank Accession Nos. J0917, M73260, X73487, AF108105, L19443, NC 003266 and NCBI Accession Nos. NC 001405, NC 001460, NC 002067, NC 00454).

Those skilled in the art will appreciate that the inventive adenovirus vectors can be modified or "targeted" as described in Douglas et al., (1996) *Nature Biotechnology* 14:1574; U.S. Pat. No. 5,922,315 to Roy et al.; U.S. Pat. No. 5,770,442 to Wickham et al.; and/or U.S. Pat. No. 5,712,136 to Wickham et al.

An adenovirus vector genome or rAd vector genome will typically comprise the Ad terminal repeat sequences and packaging signal. An "adenovirus particle" or "recombinant adenovirus particle" comprises an adenovirus vector genome or recombinant adenovirus vector genome, respectively, packaged within an adenovirus capsid. Generally, the adenovirus vector genome is most stable at sizes of about 28 kb to 38 kb (approximately 75% to 105% of the native genome size). In the case of an adenovirus vector containing large deletions and a relatively small heterologous nucleic acid of interest, "stuffer DNA" can be used to maintain the total size of the vector within the desired range by methods known in the art.

Normally, adenoviruses bind to a cell surface receptor (CAR) of susceptible cells via the knob domain of the fiber protein on the virus surface. The fiber knob receptor is a 45 kDa cell surface protein which has potential sites for both glycosylation and phosphorylation. (Bergelson et al., (1997), *Science* 275:1320-1323). A secondary method of entry for adenovirus is through integrins present on the cell surface. Arginine-Glycine-Aspartic Acid (RGD) sequences of the adenoviral penton base protein bind integrins on the cell surface.

The adenovirus genome can be manipulated such that it encodes and expresses a nucleic acid of interest but is inactivated in terms of its ability to replicate in a normal lytic viral life cycle. See, for example, Berkner et al. (1988) *BioTechniques* 6:616; Rosenfeld et al. (1991) *Science* 252:431-434; and Rosenfeld et al. (1992) *Cell* 68:143-155. Representative adenoviral vectors derived from the adenovirus strain Ad type 5 d1324 or other strains of adenovirus (e.g., Ad2, Ad3, Ad7 etc.) are known to those skilled in the art.

Recombinant adenoviruses can be advantageous in certain circumstances in that they are not capable of infecting non-dividing cells and can be used to infect a wide variety of cell types, including epithelial cells. Furthermore, the virus particle is relatively stable and amenable to purification and concentration, and can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., as occurs with retroviral DNA). Moreover, the carrying capacity of the adenoviral genome for foreign DNA is large relative to other delivery vectors (Haj-Ahmand and Graham (1986) *J. Virol.* 57:267).

In particular embodiments, the adenovirus genome contains a deletion therein, so that at least one of the adenovirus genomic regions does not encode a functional protein. For example, first-generation adenovirus vectors are typically deleted for the E1 genes and packaged using a cell that expresses the E1 proteins (e.g., 293 cells). The E3 region is also frequently deleted as well, as there is no need for complementation of this deletion. In addition, deletions in the E4, E2a, protein IX, and fiber protein regions have been described, e.g., by Armentano et al, (1997) *J. Virology* 71:2408, Gao et al., (1996) *J. Virology* 70:8934, Dedieu et al., (1997) *J. Virology* 71; 4626, Wang et al., (1997) *Gene Therapy* 4:393, U.S. Pat. No. 5,882,877 to Gregory et al. (the disclosures of which are incorporated herein in their entirety). Preferably, the deletions are selected to avoid toxicity to the packaging cell. Wang et al., (1997) *Gene Therapy* 4:393, has described toxicity from constitutive co-expression of the E4 and E1 genes by a packaging cell line. Toxicity can be avoided by regulating expression of the E1 and/or E4 gene products by an inducible, rather than a constitutive, promoter. Combinations of deletions that avoid toxicity or other deleterious effects on the host cell can be routinely selected by those skilled in the art.

As further examples, in particular embodiments, the adenovirus is deleted in the polymerase (pol), preterminal protein (pTP), IVa2 and/or 100K regions (see, e.g., U.S. Pat. No. 6,328,958; PCT publication WO 00/12740; and PCT publication WO 02/098466; Ding et al., (2002) *Mol. Ther.* 5:436; Hodges et al., *J. Virol.* 75:5913; Ding et al., (2001) *Hum Gene Ther* 12:955; the disclosures of which are incorporated herein by reference in their entireties for the teachings of how to make and use deleted adenovirus vectors for gene delivery).

The term "deleted" adenovirus as used herein refers to the omission of at least one nucleotide from the indicated region of the adenovirus genome. Deletions can be greater than about 1, 2, 3, 5, 10, 20, 50, 100, 200, or even 500 nucleotides. Deletions in the various regions of the adenovirus genome can be about at least 1%, 5%, 10%, 25%, 50%, 75%, 90%, 95%, 99%, or more of the indicated region. Alternately, the entire region of the adenovirus genome is deleted. Preferably, the deletion will prevent or essentially prevent the expression of a functional protein from that region. In general, larger deletions are preferred as these have the additional advantage that they will increase the carrying capacity of the deleted adenovirus for a heterologous nucleotide sequence of interest. The various regions of the adenovirus genome have been mapped and are understood by those skilled in the art (see, e.g., FIELDS et al., VIROLOGY, volume 2, chapters 67 and 68 (3d ed., Lippincott-Raven Publishers).

Those skilled in the art will appreciate that typically, with the exception of the E3 genes, any deletions will need to be complemented in order to propagate (replicate and package) additional virus, e.g., by transcomplementation with a packaging cell.

The present invention can also be practiced with "gutted" adenovirus vectors (as that term is understood in the art, see e.g., Lieber et al., (1996) *J. Virol.* 70:8944-60) in which essentially all of the adenovirus genomic sequences are deleted.

Adeno-associated viruses (AAV) have also been employed as nucleic acid delivery vectors. For a review, see Muzyczka et al. *Curr. Topics in Micro. and Immunol.* (1992) 158:97-129). AAV are parvoviruses and have small icosahedral virions, 18-26 nanometers in diameter and contain a single stranded genomic DNA molecule 4-5 kilobases in size. The viruses contain either the sense or antisense strand of the DNA molecule and either strand is incorporated into the virion. Two open reading frames encode a series of Rep and Cap polypeptides. Rep polypeptides (Rep50, Rep52, Rep68 and Rep78) are involved in replication, rescue and integration of the AAV genome, although significant activity can be observed in the absence of all four Rep polypeptides. The Cap proteins (VP1, VP2, VP3) form the virion capsid. Flanking the rep and cap open reading frames at the 5' and 3' ends of the genome are 145 basepair inverted terminal repeats (ITRs), the first 125 basepairs of which are capable of forming Y- or T-shaped duplex structures. It has been shown that the ITRs represent the minimal cis sequences required for replication, rescue, packaging and integration of the AAV genome. Typically, in recombinant AAV vectors (rAAV), the entire rep and cap coding regions are excised and replaced with a heterologous nucleic acid of interest.

AAV are among the few viruses that can integrate their DNA into non-dividing cells, and exhibit a high frequency of stable integration into human chromosome 19 (see, for example, Flotte et al. (1992) *Am. J. Respir. Cell. Mol. Biol.* 7:349-356; Samulski et al., (1989) J. Virol. 63:3822-3828; and McLaughlin et al., (1989) *J. Virol.* 62:1963-1973). A variety of nucleic acids have been introduced into different cell types using AAV vectors (see, for example, Hermonat et al., (1984) *Proc. Natl. Acad. Sci. USA* 81:6466-6470; Tratschin et al., (1985) *Mol. Cell. Biol.* 4:2072-2081; Wondisford et al., (1988) *Mol. Endocrinol.* 2:32-39; Tratschin et al., (1984) *J. Virol.* 51:611-619; and Flotte et al., (1993) *J. Biol. Chem.* 268:3781-3790).

A rAAV vector genome will typically comprise the AAV terminal repeat sequences and packaging signal. An "AAV particle" or "rAAV particle" comprises an AAV vector genome or rAAV vector genome, respectively, packaged within an AAV capsid. The rAAV vector itself need not contain AAV genes encoding the capsid and Rep proteins. In particular embodiments of the invention, the rep and/or cap genes are deleted from the AAV genome. In a representative embodiment, the rAAV vector retains only the terminal AAV sequences (ITRs) necessary for integration, excision, replication.

Sources for the AAV capsid genes can include serotypes AAV-1, AAV-2, AAV-3 (including 3a and 3b), AAV-4, AAV-5, AAV-6, AAV-7, AAV-8, as well as bovine AAV and avian AAV, and any other virus classified by the International Committee on Taxonomy of Viruses (ICTV) as an AAV (see, e.g., BERNARD N. FIELDS et al., VIROLOGY, volume 2, chapter 69 (4th ed., Lippincott-Raven Publishers).

Because of packaging limitations, the total size of the rAAV genome will preferably be less than about 5.2, 5, 4.8, 4.6, 4.5 or 4.2 kb in size.

Any suitable method known in the art can be used to produce AAV vectors expressing the nucleic acids encoding the components of the complex of this invention (see, e.g., U.S. Pat. Nos. 5,139,941; 5,858,775; 6,146,874 for illustrative methods). In one particular method, AAV stocks can be produced by co-transfection of a rep/cap vector encoding AAV packaging functions and the template encoding the AAV vDNA into human cells infected with the helper adenovirus (Samulski et al., (1989) *J. Virology* 63:3822).

In other particular embodiments, the adenovirus helper virus is a hybrid helper virus that encodes AAV Rep and/or capsid proteins. Hybrid helper Ad/AAV vectors expressing AAV rep and/or cap genes and methods of producing AAV stocks using these reagents are known in the art (see, e.g., U.S. Pat. Nos. 5,589,377; and 5,871,982, 6,251,677; and 6,387,368). Preferably, the hybrid Ad of the invention expresses the AAV capsid proteins (i.e., VP1, VP2, and VP3). Alternatively, or additionally, the hybrid adenovirus can express one or more of AAV Rep proteins (i.e., Rep40, Rep52, Rep68 and/or Rep78). The AAV sequences can be operatively associated with a tissue-specific or inducible promoter.

The AAV rep and/or cap genes can alternatively be provided by a packaging cell that stably expresses the genes (see, e.g., Gao et al., (1998) *Human Gene Therapy* 9:2353; Inoue et al., (1998) *J. Virol.* 72:7024; U.S. Pat. No. 5,837,484; WO 98/27207; U.S. Pat. No. 5,658,785; WO 96/17947).

Another vector for use in the present invention comprises Herpes Simplex Virus (HSV). Herpes simplex virions have an overall diameter of 150 to 200 nm and a genome consisting of one double-stranded DNA molecule that is 120 to 200 kilobases in length. Glycoprotein D (gD) is a structural component of the HSV envelope that mediates virus entry into host cells. The initial interaction of HSV with cell surface heparin sulfate proteoglycans is mediated by another glycoprotein, glycoprotein C (gC) and/or glycoprotein B (gB). This is followed by interaction with one or more of the viral glycoproteins with cellular receptors. It has been shown that glycoprotein D of HSV binds directly to Herpes virus entry mediator (HVEM) of host cells. HVEM is a member of the tumor necrosis factor receptor superfamily (Whitbeck et al., (1997), *J. Virol.;* 71:6083-6093). Finally, gD, gB and the complex of gH and gL act individually or in combination to trigger pH-independent fusion of the viral envelope with the host cell plasma membrane. The virus itself is transmitted by direct contact and replicates in the skin or mucosal membranes before infecting cells of the nervous system for which HSV has particular tropism. It exhibits both a lytic and a latent function. The lytic cycle results in viral replication and cell death. The latent function allows for the virus to be maintained in the host for an extremely long period of time.

HSV can be modified for the delivery of nucleic acids to cells by producing a vector that exhibits only the latent function for long-term gene maintenance. HSV vectors are useful for nucleic acid delivery because they allow for a large DNA insert of up to or greater than 20 kilobases; they can be produced with extremely high titers; and they have been shown to express nucleic acids for a long period of time in the central nervous system as long as the lytic cycle does not occur.

In other particular embodiments of the present invention, the delivery vector of interest is a retrovirus. Retroviruses normally bind to a virus-specific cell surface receptor, e.g., CD4 (for HIV); CAT (for MLV-E; ecotropic Murine leukemic virus E); RAM1/GLVR2 (for murine leukemic virus-A; MLV-A); GLVR1 (for Gibbon Ape leukemia virus (GALV) and Feline leukemia virus B (FeLV-B)). The development of specialized cell lines (termed "packaging cells") which produce only replication-defective retroviruses has increased the utility of retroviruses for gene therapy, and defective retroviruses are characterized for use in gene transfer for gene therapy purposes (for a review, see Miller, (1990) *Blood* 76:271). A replication-defective retrovirus can be packaged into virions which can be used to infect a target cell through the use of a helper virus by standard techniques.

Yet another suitable vector is a poxvirus vector. These viruses are very complex, containing more than 100 proteins, although the detailed structure of the virus is presently unknown. Extracellular forms of the virus have two membranes while intracellular particles only have an inner membrane. The outer surface of the virus is made up of lipids and proteins that surround the biconcave core. Poxviruses are antigenically complex, inducing both specific and cross-reacting antibodies after infection. Poxvirus receptors are not presently known, but it is likely that there exists more than one given the tropism of poxvirus for a wide range of cells. Poxvirus gene expression is well studied due to the interest in using vaccinia virus as a vector for expression of nucleic acids.

In addition to viral transfer methods, such as those illustrated above, non-viral methods can also be employed. Many non-viral methods of nucleic acid transfer rely on normal mechanisms used by mammalian cells for the uptake and intracellular transport of macromolecules. In particular embodiments, non-viral nucleic acid delivery systems rely on endocytic pathways for the uptake of the nucleic acid molecule by the targeted cell. Exemplary nucleic acid delivery systems of this type include liposomal derived systems, polylysine conjugates, and artificial viral envelopes.

Plasmid vectors can be used in the practice of the present invention. Naked plasmids can be introduced into muscle cells by injection into the tissue. Expression can extend over many months, although the number of positive cells is typically low (Wolff et al., (1989) *Science* 247:247). Cationic lipids have been demonstrated to aid in introduction of nucleic acids into some cells in culture (Felgner and Ringold, (1989) *Nature* 337:387). Injection of cationic lipid plasmid DNA complexes into the circulation of mice has been shown to result in expression of the DNA in lung (Brigham et al., (1989) *Am. J. Med. Sci.* 298:278). One advantage of plasmid DNA is that it can be introduced into non-replicating cells.

V. Expression Systems for the Reconstituted Complex

As indicated above, the components of the reconstituted complex can be produced in, and optionally purified from, cultured cells or organisms expressing one or more heterologous nucleic acids encoding the proteins of the complex for a variety of purposes (e.g., screening assays to identify compounds for modulating HTMase activity or cancer, detecting cancer, large-scale protein production and/or research purposes).

Generally, the isolated nucleic acid is incorporated into an expression vector (viral or nonviral as described above). Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding an EED, EZH2, SUZ12, RbAp48 and/or AEBP2 subunit operatively associated with the promoter, and, optionally, a termination sequence including a stop signal for RNA polymerase and a polyadenylation signal for polyadenylase.

Expression vectors can be designed for expression of polypeptides in prokaryotic or eukaryotic cells. For example, polypeptides can be expressed in bacterial cells such as *E. coli*, insect cells (e.g., in the baculovirus expression system), yeast cells or mammalian cells. Some suitable host cells are discussed further in Goeddel, *Gene Expression Technology*: Methods in Enzymology 185, Academic Press, San Diego, Calif. (1990). Examples of vectors for expression in yeast *S. cerevisiae* include pYepSecl (Baldari et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.). Baculovirus vectors available for expression of nucleic acids to produce proteins in cultured insect cells (e.g., Sf 9 cells) are described above and include the pAc series (Smith et al., (1983) *Mol. Cell. Biol.* 3:2156-2165) and the pVL series (Lucklow, V. A., and Summers, M. d. (1989) *Virology* 170:31-39).

Examples of mammalian expression vectors include pCDM8 (Seed, (1987) *Nature* 329:840) and pMT2PC (Kaufman et al. (1987), *EMBO J.* 6:187-195). When used in mammalian cells, the expression vector's control functions are often provided by viral regulatory elements. For example, commonly used promoters are derived from polyoma, adenovirus 2, cytomegalovirus and Simian Virus 40.

Vectors can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al. (Molecular Cloning: A Laboratory Manual, 2nd Edition, Cold Spring Harbor Laboratory press (1989)), and other laboratory manuals.

When producing stably transformed cells, often only a small fraction of cells (in particular, mammalian cells) integrate a foreign DNA into their genome. In order to identify and select these integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

Recombinant proteins can also be produced in a transgenic plant in which the isolated nucleic acid encoding the protein is inserted into the nuclear or plastidic genome. Plant transformation is known as the art. See, in general, *Methods in Enzymology* Vol. 153 ("Recombinant DNA Part D") 1987, Wu and Grossman Eds., Academic Press and European Patent Application EP 693554.

Foreign nucleic acids can be introduced into plant cells or protoplasts by several methods. For example, nucleic acid can be mechanically transferred by microinjection directly into plant cells by use of micropipettes. Foreign nucleic acid can also be transferred into a plant cell by using polyethylene glycol which forms a precipitation complex with the genetic material that is taken up by the cell (Paszkowski et al. (1984) *EMBO J.* 3:2712-22). Foreign nucleic acid can be introduced into a plant cell by electroporation (Fromm et al. (1985) *Proc. Natl. Acad. Sci. USA* 82:5824). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells comprising the foreign nucleic acid can be accomplished using phenotypic markers.

Cauliflower mosaic virus (CaMV) can be used as a vector for introducing foreign nucleic acids into plant cells (Hohn et al. (1982) "Molecular Biology of Plant Tumors," Academic Press, New York, pp. 549-560; Howell, U.S. Pat. No. 4,407, 956). CaMV viral DNA genome is inserted into a parent bacterial plasmid creating a recombinant DNA molecule which can be propagated in bacteria. The recombinant plasmid can be further modified by introduction of the desired DNA sequence. The modified viral portion of the recombinant plasmid is then excised from the parent bacterial plasmid, and used to inoculate the plant cells or plants.

High velocity ballistic penetration by small particles can be used to introduce foreign nucleic acid into plant cells. Nucleic acid is disposed within the matrix of small beads or particles, or on the surface (Klein et al. (1987) *Nature* 327:70-73). Although typically only a single introduction of a new nucleic acid segment is required, this method also provides for multiple introductions.

A nucleic acid can be introduced into a plant cell by infection of a plant cell, an explant, a meristem or a seed with *Agrobacterium tumefaciens* transformed with the nucleic acid. Under appropriate conditions, the transformed plant cells are grown to form shoots, roots, and develop further into plants. The nucleic acids can be introduced into plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al. (1984) "Inheritance of Functional Foreign Genes in Plants," *Science* 233: 496498; Fraley et al. (1983) *Proc. Natl. Acad. Sci. USA* 80:4803).

The present invention is explained in greater detail in the following non-limiting Examples.

EXAMPLE 1

Materials and Methods

Purification of Recombinant EED-EZH2 Complex and Subcomplexes. Ezh2 cDNA was cloned into BamHI and XhoI sites pFASTBAC™ (INVITROGEN™, Carlsbad, Calif.) without FLAG®. EED cDNA was cloned into EcoRI and XhoI sites of an N-terminal FLAG®-tagged vector pFASTBAC™, SUZ12 and AEBP2 cDNAs were inserted into EcoRI and NotI sites of the same vector. Baculovirus for RbAp48 are established in the art (Zhang, et al. (1999) *Genes Dev.* 13:1924-1935). Each baculovirus expressing a different component was generated and amplified following the manufacturer's protocol. To purify the recombinant EED-EZH2 complex, different baculoviruses were used to co-infect SF9 cells. After two days of infection, cells were collected and resuspended in F lysis buffer (20 mM Tris, pH 7.9, 500 mM NaCl, 4 mM MgCl$_2$, 0.4 mM EDTA, 2 mM DTT, 20% glycerol, 0.1% NP-40) with proteinase inhibitors. Cells were homogenized with a pestle three times (10 strokes each) in a period of 30 minutes. The supernatant was recovered by centrifuging at 11,000 rpm for 10 minutes. The supernatant was adjusted to 300 mM NaCl by adding dilution buffer (20 mM Tris, pH 7.9, 10% glycerol), then incubated with the M2 α-FLAG® agarose (Sigma, St. Louis, Mo.) equilibrated with F lysis buffer for 4 hours at 4° C. Upon removal of all unbound protein with F washing buffer (20 mM Tris, pH 7.9, 150 mM NaCl, 2 mM MgCl$_2$, 0.2 mM EDTA, 1 mM DTT, 15% glycerol, 0.01% NP-40), bound proteins were eluted with FLAG® peptide (0.2 mg/mL) for 20 minutes at room temperature, then the eluted complexes were further purified through a gel-filtration S200 or SUPEROSE® 6 column. Using this protocol, milligram quantities of reconstituted complex were generated. Moreover, while co-expression resulted in an active, reconstituted EED-EZH2 complex, expression of each component separately (i.e., in individual cells) and subsequent mixing was not found to produce an active complex.

HMTase Assay, Substrate Preparation, and Antibodies. Histone methylation assays were performed in accordance with well-established methods (Wang, et al. (2001) *Science* 293:853-857). Substrates for the HMTase assay including oligonucleosomes, mononucleosomes, and core histone were purified from chicken blood using established protocols (Fang, et al. (2003) *Methods Enzymol.* 377:213-226). Wild-type and mutant recombinant histone H3 were expressed and purified according to known methods (Cao, et al. (2002) *Science* 298:1039-1043). Antibodies against EZH2, SUZ12, 2mK27, 3mK27, 3mK9, and 1mK27 are known (Cao, et al. (2002) *Science* 298:1039-1043; Peters, et al. (2003) *Mol. Cell* 12:1577-1589; Plath, et al. (2003) *Science* 300:131-135).

Plasmids and GST Pull-Down Assay. Full-length AEBP2 cDNA was cloned by PCR amplification from a HeLa cDNA library and the sequence was verified by DNA sequence analysis. Full-length cDNAs for Ezh2, EED, SUZ12, RbAp48, AEBP2 and their deletions were inserted into pCITE® vector for in vitro translation using the rabbit reticulocyte lysate kit according to the manufacturer's instructions (PROMEGA®, Madison, Wis.). Full-length cDNAs for SUZ12, EED, RbAp48 and AEBP2 were also cloned into pGEX-KG vector for the production of GST-fusion proteins. About 3 μg of GST or GST fusion proteins were bound to 10 μL of glutathione-immobilized agarose beads (Sigma, St. Louis, Mo.) and incubated with in vitro-translated products in 500 μL buffer A (50 mM Tris-HCl, pH 7.9, 0.5 mM EDTA, 1 mM dithiothreitol, 0.2 mM phenylmethylsulfonyl fluoride, 10% glycerol) containing 150 mM KCl and 0.05% NP-40. After incubation at 4° C. for 2 hours, the beads were washed three times with buffer A containing 300 mM KCl and 0.05% NP-40 and then washed once in buffer A containing 50 mM KCl before being subjected to SDS-PAGE and autoradiogram analysis.

SUZ12 Knock-Down Cell Line and Growth Analyses. HeLa cells were cultured in Dulbecco's Modified Eagle Medium (DMEM) supplied with 10% fetal bovine serum (FBS). A desired 64-bp oligonucleotide that targets SUZ12 was cloned into pHTPsiRNA vector (Wang, et al. (2003) *Mol. Cell* 12:475-487). The two oligonucleotides used in generating the stem-loop RNA that target SUZ12 were 5'-GAT CCC CGTCGCAACGGACCAGTTAA T TCA AGA GA TTAACTGGTCCGTTGCGAC TTT TTG GAA A-3' (SEQ ID NO:1) and 5'-TCG ATT TCC AAA AA GTCGCAACGGACCAGTTAA TCT CTT GAA TTAACTGGTCCGTTGCGACGG G-3' (SEQ ID NO:2), wherein stem structures are underlied. The SUZ12 siRNA vector was transfected into HeLa cells by EFFECTENE® (INVITROGEN™, Carlsbad, Calif.). Stable transfectants were selected in the presence of 2 μg/mL puromycin. Cells derived from these transfectants were used for western blot analysis and real-time RT-PCR analysis. For cell growth analyses, 4×10$^4$ cells were seeded in 12-well plates. After 24, 48 and 96 hours in culture, cells were trypsinized, collected in triplicate, and counted by trypan-blue staining.

Real-Time PCR and ChIP Assays. Real-time PCR was performed in triplicate using SYBR® Green PCR Master Mix and the ABI prism 7900 sequence detection system. Quantitative PCR reactions were performed under conditions standardized for each primer. Standard curves were generated using 10-fold dilutions of standard plasmids. To compare the relative amount of target in different samples, all values were normalized to the appropriately quantified GAPDH control. The primers used in quantitative PCR were: SUZ12 cDNA primers 5'-AAA CGA AAT CGT GAG GAT GG-3' (SEQ ID NO:3) and 5'-CCA TTT CCT GCA TGG CTA CT-3' (SEQ ID NO:4); HoxC6 cDNA primers 5'-CCA GGA CCA GAA AGC CAG TA-3' (SEQ ID NO:5) and 5'-GGT CTG GTA CCG CGA GTA GA-3' (SEQ ID NO:6); HoxC8 cDNA primers 5'-CTC AGG CTA CCA GCA GAA CC-3' (SEQ ID NO:7) and 5'-GAG CCC CAT AAA GGG ACT GT-3' (SEQ ID NO:8); and HoxA9 cDNA primers 5'-TGC AGC TTC CAG TCC AAG G-3' (SEQ ID NO:9) and 5'-GTA GGG GTG GTG GTG ATG GT-3' (SEQ ID NO:10).

For ChIP assays, approximately 2×10$^6$ HeLa cells in 150-mm dishes were treated with DMEM containing 1% formaldehyde for 10 minutes. Crosslinking was stopped by the addition of 0.125 M glycine for 10 minutes. After washing twice with phosphate-buffered saline (PBS), the cells were resuspended in 300 μL of cell lysis buffer (10 mM HEPES, pH 7.9, 0.5% NP-40, 1.5 mM MgCl$_2$, 10 mM KCl, 0.5 mM DTT) and held on ice for 10 minutes. The cells were subsequently centrifuged at 4,000 rpm for 5 minutes, resuspended in nuclear lysis buffer (20 mM HEPES, pH 7.9, 25% glycerol, 0.5% NP-40, 0.42 M NaCl, 1.5 mM MgCl$_2$, 0.2 mM EDTA) containing protease inhibitors, and incubated at 4° C. for 20 minutes to extract nuclear proteins. Extracted chromatin was sonicated into fragments having an average length of 0.5-3 kb. After centrifugation at 13,000 rpm for 10 minutes, the supernatants were diluted in an equal volume of dilution buffer containing 1% TRITON® X-100, 2 mM EDTA, 20 mM Tris-HCl, pH 7.9, 50 mM NaCl, and protease inhibitors. ChIP assays were then performed with indicated antibodies. ChIP DNA was detected using standard PCR with the following primer pairs for the four different regions in HoxA9: A, 5'-TCC ACC TTT CTC TCG ACA GCA C-3' (SEQ ID NO:11) and 5'-GTG GGA GGC TCA GGA TGG AAG-3' (SEQ ID NO:12); B, 5'-TCG CCA ACC AAA CAC AAC AGT C-3' (SEQ ID NO:13) and 5'-AAA GGG ATC GTG CCG CTC TAC-3' (SEQ ID NO:14); C, 5'-CTC ACC GAG AGG CAG GTC AAG-3' (SEQ ID NO:15) and 5'-AGC CTA CCA TCA ACA GTT GTG C-3' (SEQ ID NO:16); D, 5'-GAA CGG CCA CAA CTT CGG AGG-3' (SEQ ID NO:17) and 5'-CCG GGG AGT CTG CGT GGA G-3' (SEQ ID NO:18).

EXAMPLE 2

Reconstituted EED-EZH2 Complex Enzymatic Activity and Substrate Specificity

A multi-subunit EED-EZH2/ESC-E(Z) complex, purified from HeLa cell and *Drosophila* embryos was found to methylate nucleosomal histone H3 at lysine 27 (Cao, et al. (2002)

Figure 1B:
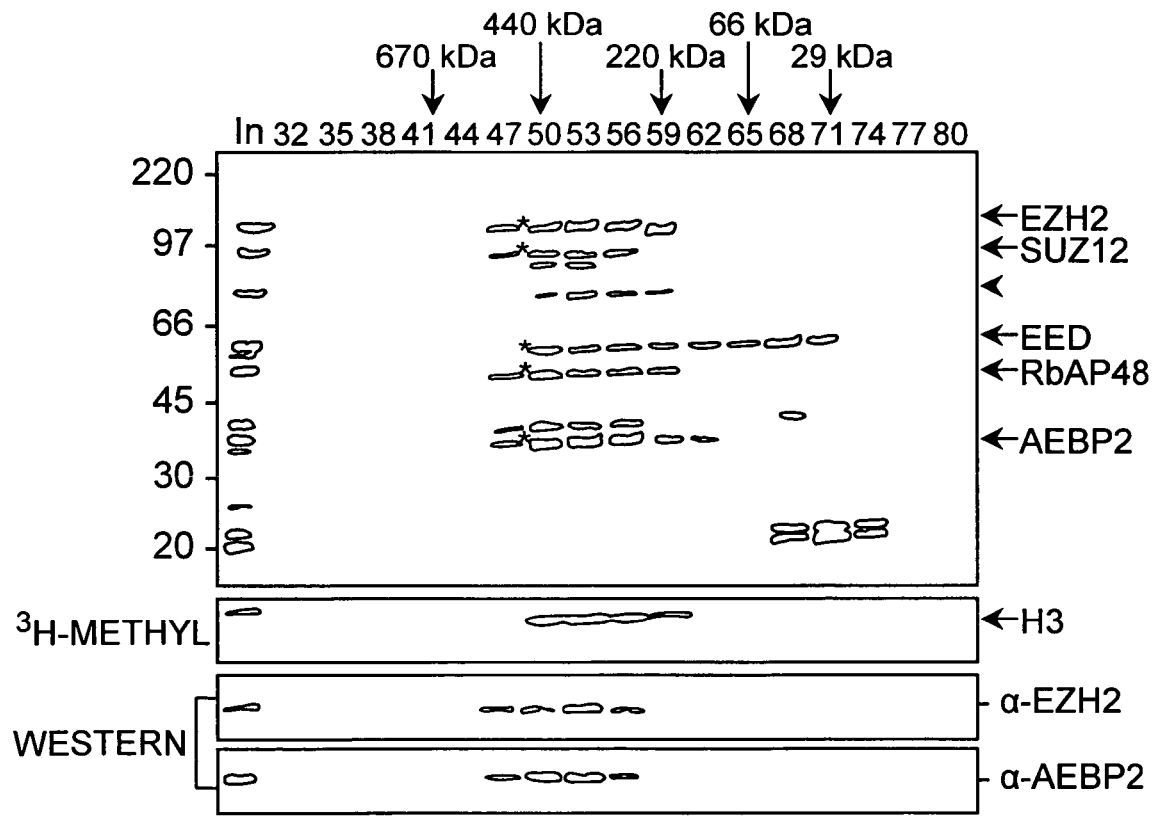
Figure 1C:
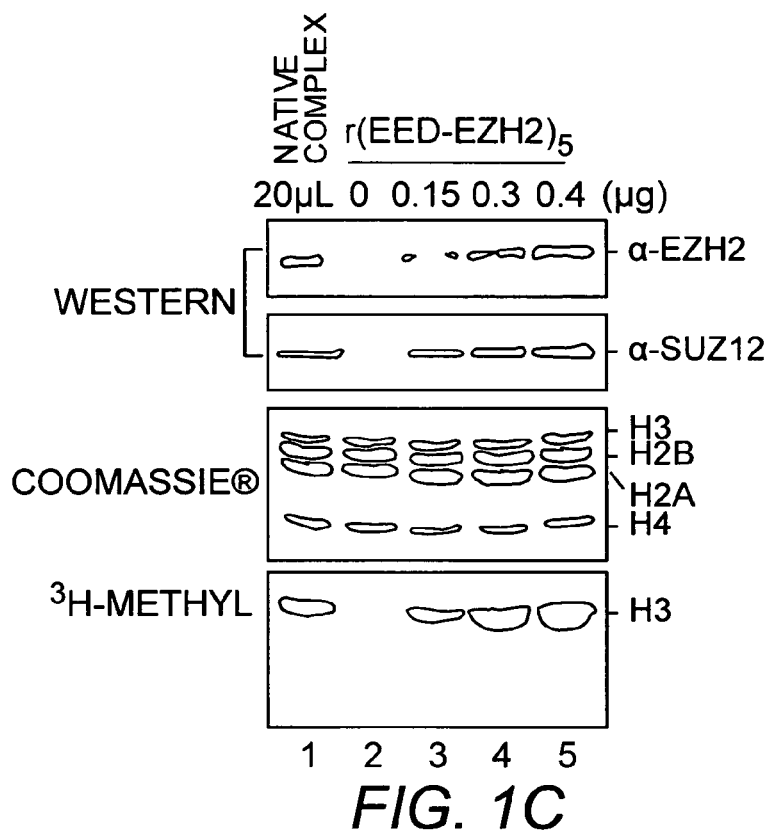
Figure 1D:
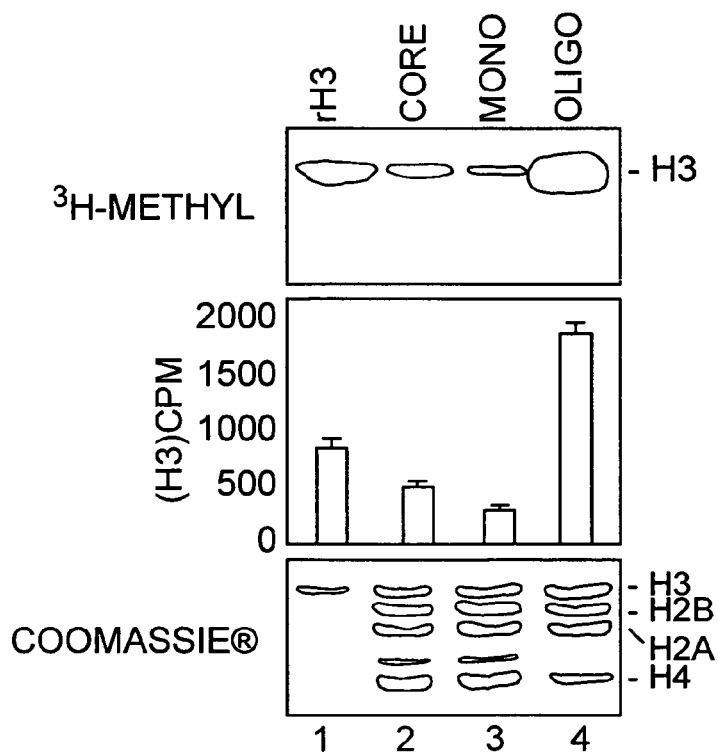

Science 298:1039-1043; Czermin, et al. (2002) Cell 111:185-196; Kuzmichev, et al. (2002) Genes Dev. 16:2893-2905; Muller, et al. (2002) Cell 111:197-208). The EED-EZH2 complex was found to be composed of EZH2, SUZ12, EED, RbAp48, and AEBP2 (Cao, et al. (2002) Science 298:1039-1043). To dissect the function of individual subunits and to obtain large amounts of purified enzyme complex for detailed functional analyses, it was determined whether the enzymatic activity could be reconstituted using recombinant proteins. To this end, Sf9 cells were co-infected with baculoviruses expressing FLAG®-EED; EZH2, SUZ12, RbAp48, and AEBP2. FLAG®-EED and associated proteins were purified by affinity chromatography followed by gel filtration through which free FLAG®-EED and partial complex were removed from the five-component complex (FIG. 1A). Histone methyltransferase assay and silver staining of an SDS-polyacrylamide gel containing the column fractions indicated that the five components co-purify with the enzymatic activity as a protein complex of about 400 kDa (FIG. 1B). To assess the HMTase activity of the reconstituted complex relative to that of the native EED-EZH2 complex, the fractions between 50 and 53 were pooled and different amounts of the pooled recombinant complex were compared with fixed amounts of the native EED-EZH2 complex. Results shown in FIG. 1C demonstrate that the reconstituted complex and the native complex had comparable HMTase activity when equal amounts of enzyme were compared (lane 1 with lanes 3 and 4). To characterize the reconstituted complex further, different forms of histone H3 were subjected to methylation. As with native complex (Cao, et al. (2002) Science 298:1039-1043), the preferred substrate for the reconstituted enzyme complex was histone H3 in oligonucleosome form (FIG. 1D). Moreover, a reconstituted complex containing other isoforms of EED (Kuzmichev, et al. (2004) Mol. Cell 14(2):183-93) exhibits HMTase activity. Accordingly, a reconstituted EED-EZH2 complex and a native complex have similar enzymatic activity and substrate specificity.

EXAMPLE 3

Physical Relationship Among Components of the EED-EZH2 Complex

Figure 2A:
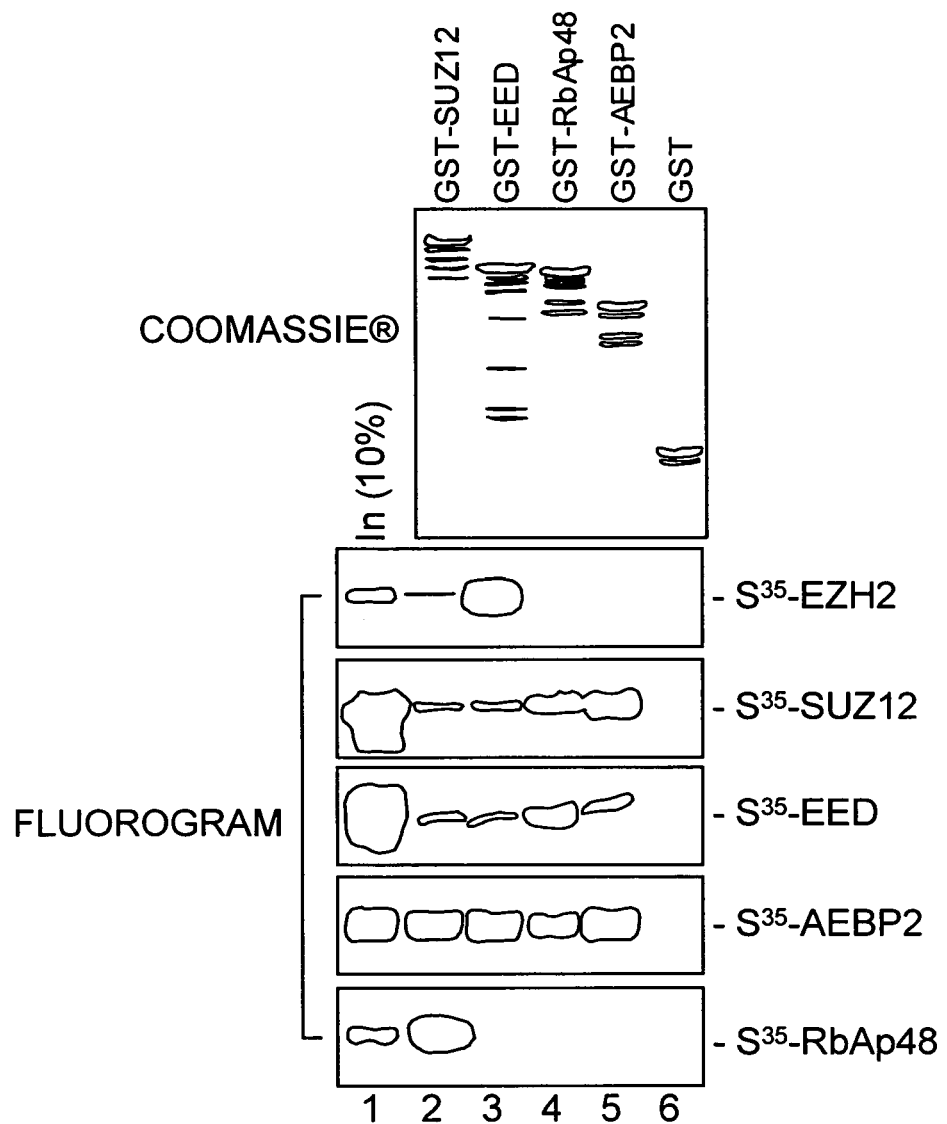
FIGS. 2A through 2C demonstrate protein-protein interactions among components of the EED-EZH2 complex.
Figure 2B:
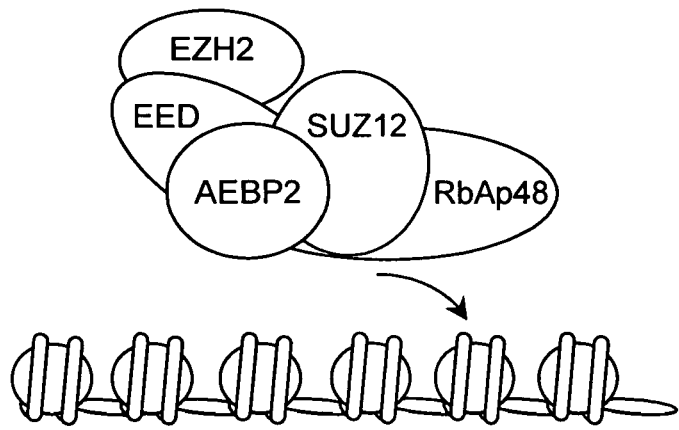

Of the five components present in the complex, EZH2 is believed to be the catalytic subunit because it is a SET-domain containing protein. It is known that EZH2 and EED interact directly (Sewalt, et al. (1998) Mol. Cell Biol. 18:3586-3595; van Lohuizen, et al. (1998) Mol. Cell Biol. 18:3572-3579); therefore, the precise spatial relationship among components of the complex and subcomplexes was determined. Towards this end, individual components, with the exception of EZH2 which could not be expressed in *E. coli*, were expressed as GST fusion proteins and used in GST pull-down assays. Consistent with previous reports (Sewalt, et al. (1998) Mol. Cell Biol. 18:3586-3595; van Lohuizen, et al. (1998) Mol. Cell Biol. 18:3572-3579), EZH2 was found to interact strongly with EED but it did not seem to directly contact any of the other subunits under these assay conditions (FIG. 2A, panel 2). In addition to EZH2, EED also interacted with SUZ12 and AEBP2 (FIG. 2A, lane 3). RbAp48 appeared to strongly interact with SUZ12 (FIG. 2A, last panel, lane 2) and weakly with AEBP2 and EED (FIG. 2A, panels 4 and 5, lane 4). Unexpectedly, AEBP2 was capable of self-association (FIG. 2A, panel 5, lane 5), and this ability appeared to be important for its interaction with RbAp48 since immobilized GST-RbAp48 could pull-down AEBP2 (FIG. 2A, panel 4, lane 4), but immobilized GST-AEBP2, which could not self-associate, could not pull-down RbAp48 (FIG. 2A, last panel, lane 5). All the interactions were specific, as parallel pull-down assays using GST alone failed to detect the interactions (FIG. 2A, lane 6). These interaction studies indicate that EZH2 associates with other components through EED, which in turn interacts with SUZ12 and AEBP2, both of which can interact with RbAp48 (FIG. 2B).

Figure 2C:
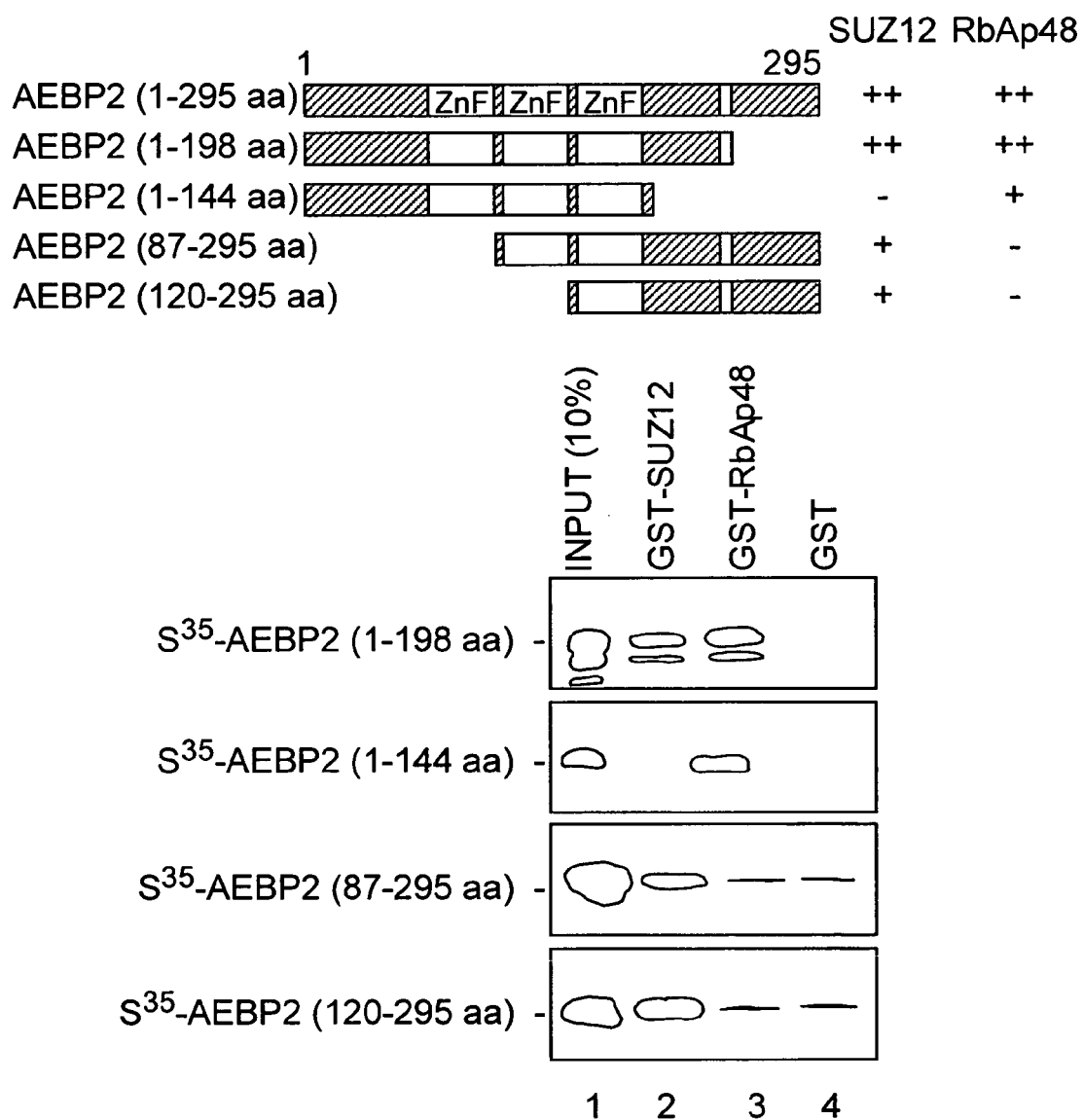

AEBP2 is a zinc-finger protein originally identified as a transcriptional repressor (He, et al. (1999) J. Biol. Chem. 274:14678-14684). Although it was identified as an integral component in a purified EED-EZH2 complex (Cao, et al. (2002) Science 298:1039-1043), it was not present in a similar purified complex (Kuzmichev, et al. (2002) Genes Dev. 16:2893-2905). Given its ability to incorporate into the complex (FIG. 1B) and to interact with multiple subunits of the complex (FIG. 2A, panel 5), the interaction of AEBP2 with SUZ12 and RbAp48 was further characterized. GST pull-down assays, using in vitro transcribed/translated full-length and deletion mutants of AEBP2, demonstrated that the N-terminal region of AEBP2 (residues 1-87) was involved in the RbAp48 interaction (FIG. 2C, compare the middle two panels), while a C-terminal region (residues 144-198) was involved in the SUZ12 interaction (FIG. 2C, compare the first two panels). These studies, in combination with the functional studies disclosed herein, indicate that AEBP2 is an integral component of the EED-EZH2 complex.

EXAMPLE 4

AEBP2 Stimulates and SUZ12 is Required for HMTase Activity

Figure 3A:
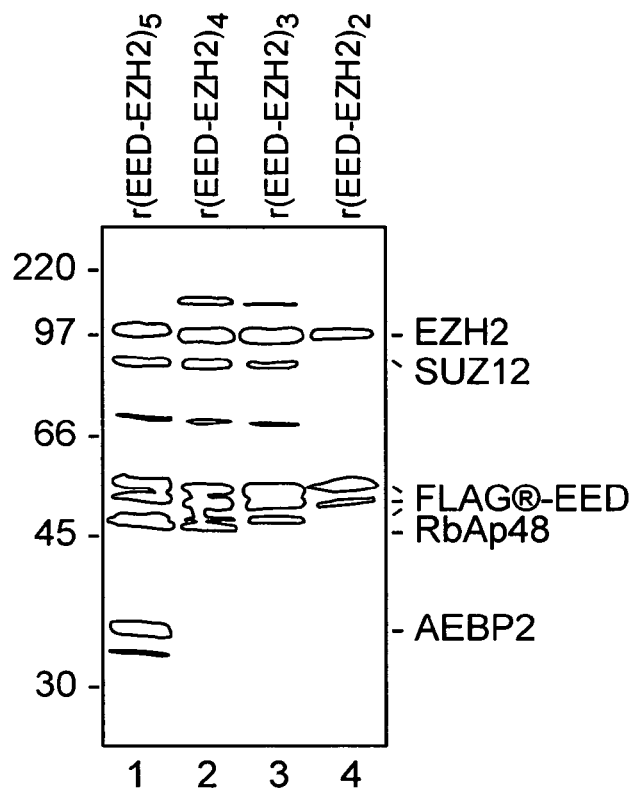
FIG. 3A through 3C show the characterization of the EED-EZH2 complex and sub-complexes.
Figure 3B:
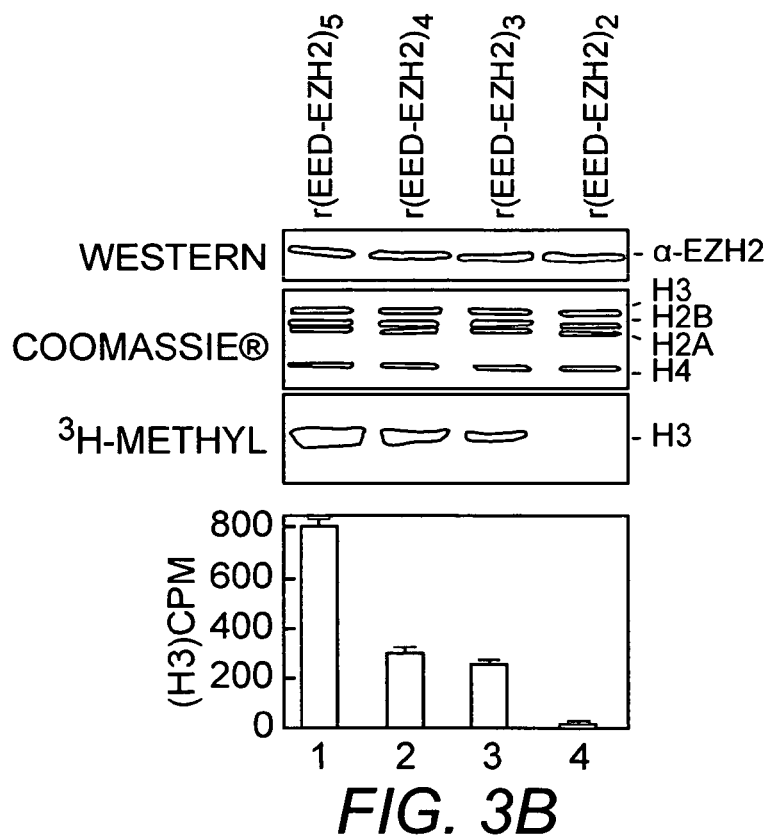
Figure 3C:
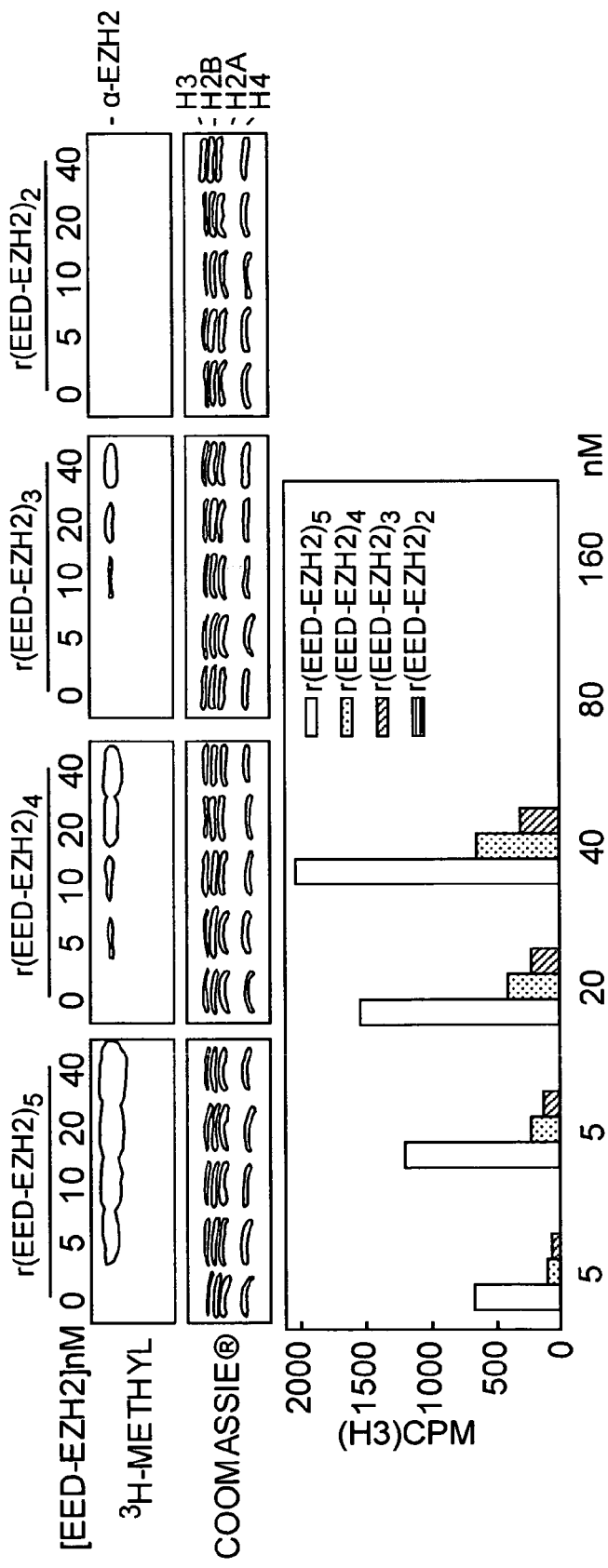

Having defined the spatial relationship among the five components, the minimum components required for the enzymatic activity were determined. Given that Ezh2 and Eed are both required for histone H3-K27 methylation in vivo (Erhardt, et al. (2003) Development 130:4235-4248; Su, et al. (2003) Nature Immunology 4(2):124-3), and based on the physical interactions defined in FIG. 2, subcomplexes were reconstituted by omitting AEBP2, RbAp48 and SUZ12 individually or in combination. Using a two-step purification procedure similar to that outlined in FIG. 1A, EED-EZH2 sub-complexes with four (omit AEBP2), three (omit AEBP2 and RbAp48), and two (omit AEBP2, RbAp48, and SUZ12) components were reconstituted. Silver staining revealed that these reconstituted sub-complexes were near homogeneity (FIG. 3A). To evaluate the relative HMTase activities of these purified complexes, equal molar amounts of the complexes, as indicated by western blot analysis of EZH2 (FIG. 3B, top panel), were used to methylate equal amounts of nucleosomal substrates (FIG. 3B, second panel). Results shown in FIG. 3B (bottom two panels) indicate that a minimum of three components containing EED, EZH2, and SUZ12 were required for the HMTase activity (compare lanes 3 and 4). Addition of RbAp48 to the three-component complex increased the incorporation of SUZ12 (FIG. 3A, compare lanes 2 and 3), resulting in an increased enzymatic activity, particularly at a higher enzyme concentration (FIG. 3C). Addition of AEBP2 to the four-component complex significantly increased the HMTase activity (FIG. 3B, compare lanes 1 and 2). Co-infection of EED, EZH2, and RbAp48 failed to form a stable complex (data not shown), indicating that incorporation of RbAp48 into the complex depends on its interaction with SUZ12 (FIG. 2A). In addition, omission of SUZ12 also failed to form a four-component complex.

HMTase activity of the reconstituted complexes was evaluated using a wide range of enzyme concentrations (FIG. 3). Although significant HMTase activity was detected at 5 nM enzyme concentration when the five-component complex was used, no activity was detected when the two-component complex was used even at a 160 nM enzyme concentration level. A significant difference in enzymatic activity was observed when the five-component and four-component complexes were compared. Thus, EZH2, EED, and SUZ12 are the minimum components required for HMTase activity and AEBP2 stimulates the HMTase activity of the four-component EED-EZH2 complex.

EXAMPLE 5

Reconstituted EED-EZH2 Complexes Methylate Nucleosomal Histone H3 at Lysine 27

Figure 4A:
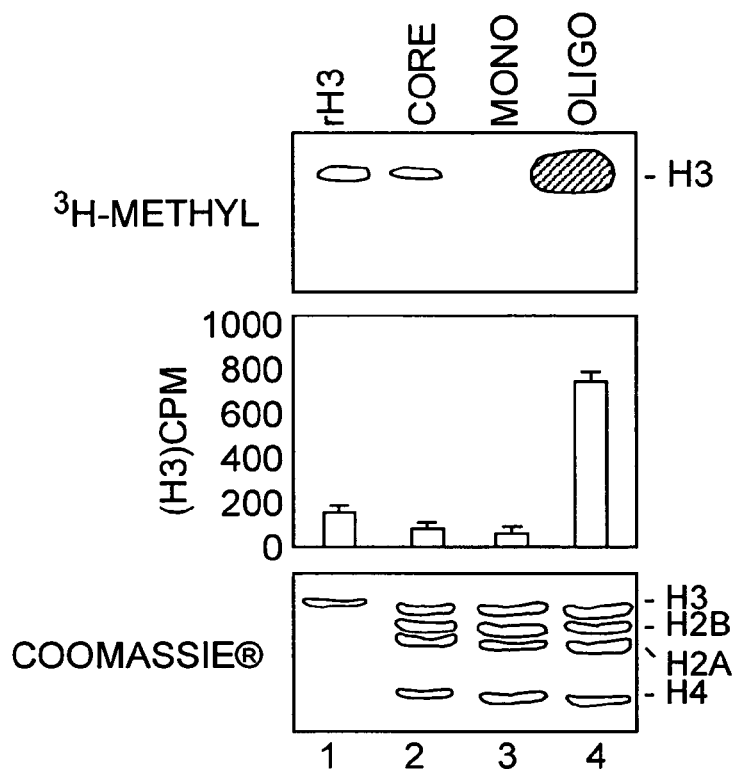
FIGS. 4A through 4B demonstrate substrate preference and site-specificity of the reconstituted EED-EZH2 enzyme complexes.

Independent purification and characterization of EED-EZH2/ESC-E(Z) HMTase complexes has been conducted (Cao, et al. (2002) Science 298:1039-1043; Czermin, et al. (2002) Cell 111:185-196; Kuzmichev, et al. (2002) Genes Dev. 16:2893-2905; Muller, et al. (2002) Cell 111:197-208). However, the properties of these purified enzyme complexes appear to have some differences. For example, while one purified EED-EZH2 complex has been shown to have a clear preference for oligonucleosome over octomer substrates (Cao, et al. (2002) Science 298:1039-1043), a similar HeLa complex devoid of AEBP2 has been shown to have the opposite preference (Kuzmichev, et al. (2002) Genes Dev. 16:2893-2905). To determine whether the presence of AEBP2 in the complex could alter the substrate preference, substrate preference was analyzed using the reconstituted EED-EZH2 complex devoid of AEBP2. Results shown in FIG. 4A indicate that, like the AEBP2-containing complex (FIG. 1D), the four-component EED-EZH2 complex also shows clear preference for oligonucleosome over octomer. Similar substrate preference was also observed with the three-component EED-EZH2 complex (data not shown). Therefore, while neither AEBP2 nor RbAp48 are involved in substrate-specificity determination, EZH2 or its associated EED and SUZ12 appear to be involved in this process.

Figure 4B:
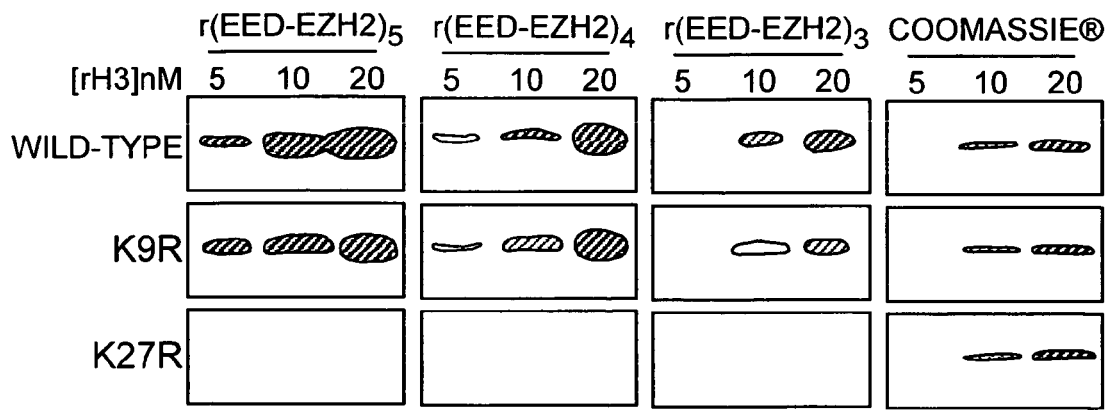

In addition to substrate preference, there is also some discrepancy about the lysine residues that the enzyme complexes methylate. Although the human EED-EZH2 complex, and its Drosophila ESC-E(Z) counterpart, were reported to methylate histone H3-K27 only (Cao, et al. (2002) Science 298:1039-1043; Muller, et al. (2002) Cell 111:197-208), histone H3-K9 HMTase activity was also reported for similar complexes (Czermin, et al. (2002) Cell 111:185-196; Kuzmichev, et al. (2002) Genes Dev. 16:2893-2905). This discrepancy is likely the result of either subtle differences in the complex composition, for example the presence or absence of AEBP2, or the minor histone H3-K9 HMTase activity was due to contamination. To differentiate these two possibilities, it was determined which lysine residues were methylated by the different reconstituted complexes. To this end, three levels of recombinant wild-type or mutant histone H3 were subjected to a histone methyltransferase assay using the enzyme complexes containing five, four, or three components. As with the native complex (Cao, et al. (2002) Science 298:1039-1043), mutation on K27 resulted in undetectable HMTase activity for the five-component complex (FIG. 4B, left column). Similar results were obtained when the four or three-component complex was used (FIG. 4B, middle two panels). Therefore, AEBP2 does not limit the ability of the four-component EED-EZH2 complex to methylate histone H3-K9; however, mutation on histone H3-K9 does appear to cause a small reduction in the ability of histone H3 to serve as a substrate for the reconstituted EED-EZH2 complexes.

EXAMPLE 6

SUZ12 Contributes to Histone H3-Lysine 27 Trimethylation In Vivo

Figure 5A:
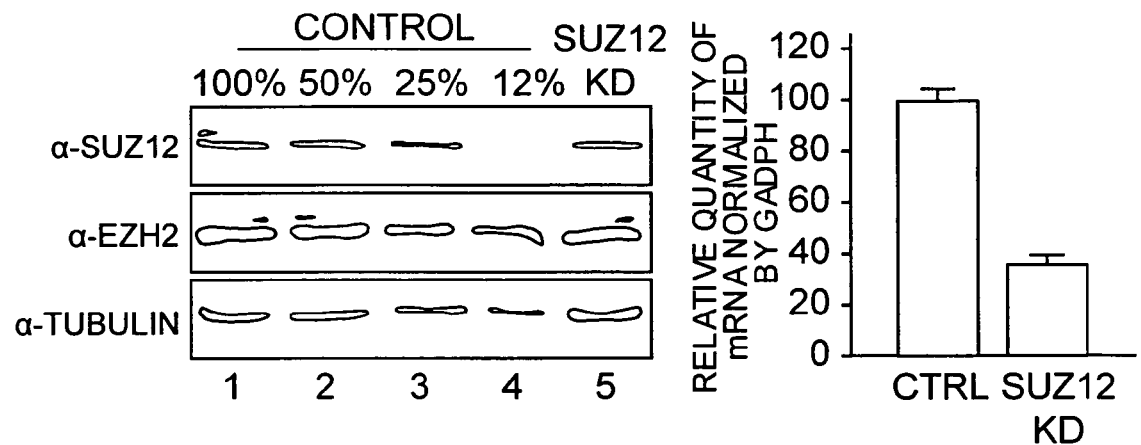
FIGS. 5A through 5C demonstrate that SUZ12 is important for cell growth and histone H3-K27 methylation in vivo.
Figure 5B:
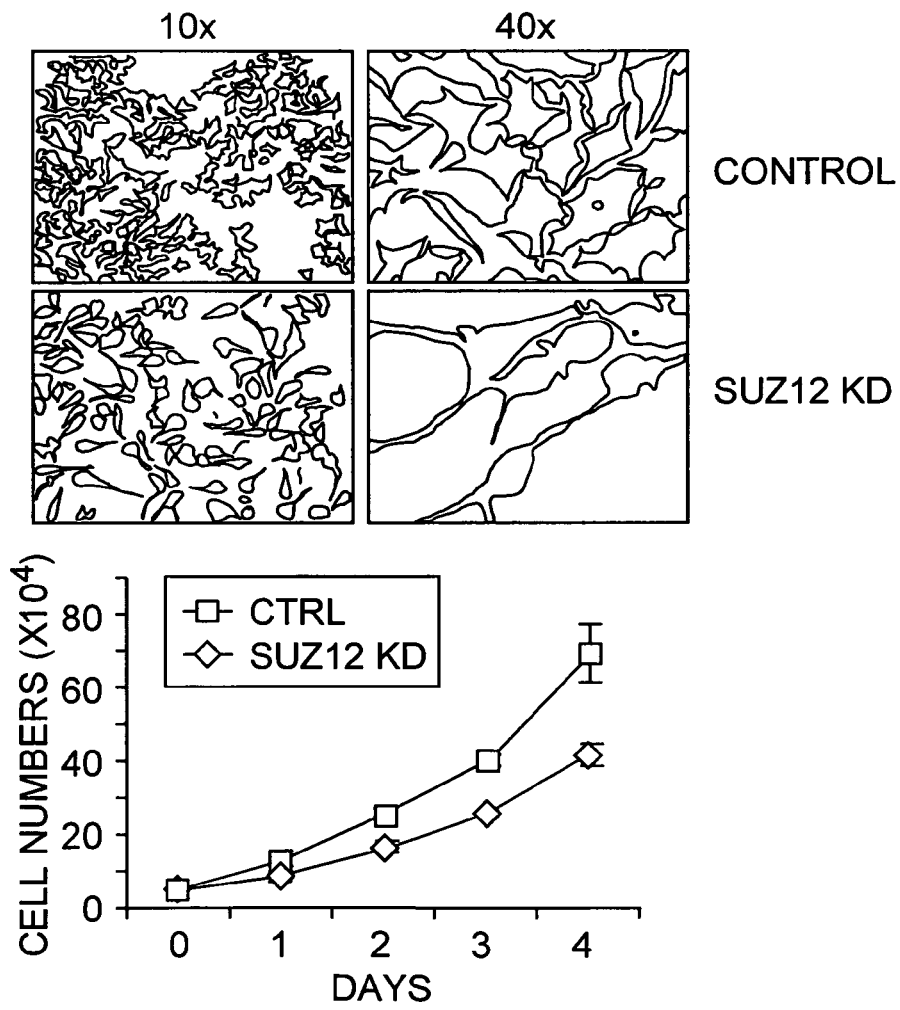
Figure 5C:
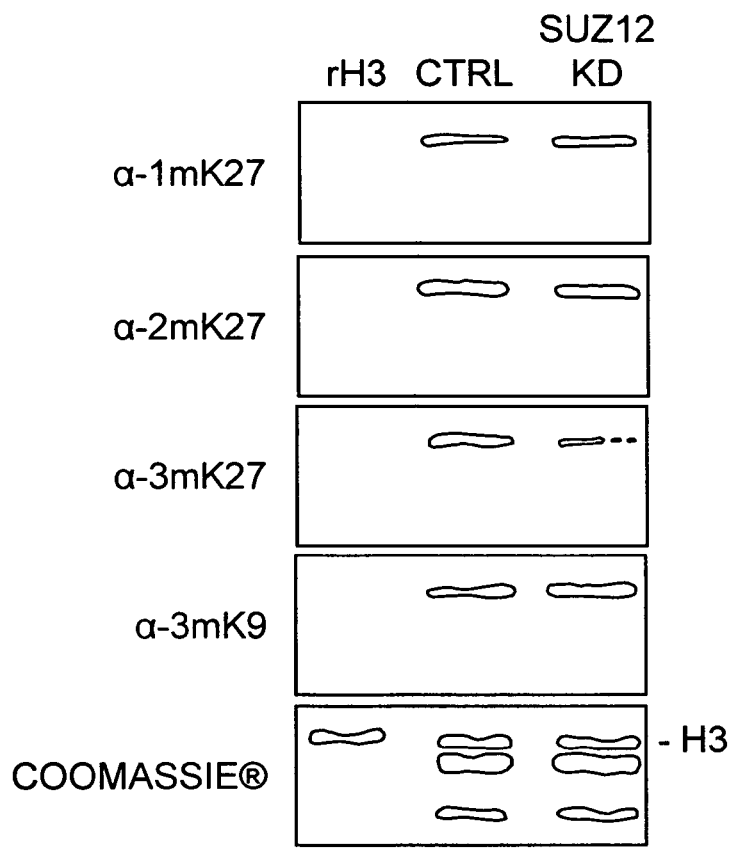

Having established a role for SUZ12 in histone H3-K27 methylation in vitro, the in vivo function was analyzed. A stable SUZ12 knock-down cell line was generated using a vector-based siRNA approach (see, e.g., Wang, et al. (2003) Mol. Cell 12:475-487). Characterization of the cell line indicated that about 75% knock-down was achieved at the protein level (FIG. 5A, compare lanes 3 and 5). Quantitative RT-PCR revealed that about 65% knock-down was achieved at the mRNA level (FIG. 5A, right panel). Like that of siRNA transfection for the EZH2 and EED components of the EED-EZH2 complex (Bracken, et al. (2003) EMBO J. 22:5323-5335; Varambally, et al. (2002) Nature 419: 624-9), vector-based SUZ12 knock-down resulted in changes in cellular morphology and growth (FIG. 5B). To evaluate the effects of SUZ12 knock-down on histone H3-K27 methylation in vivo, equivalent amounts of histones, isolated from the SUZ12 knock-down cells and cells from a parallel empty vector transfection, were subjected to western blot analysis using antibodies specific for methylated lysine 9 or lysine 27 of histone H3. Results shown in FIG. 5C indicated that SUZ12 knock-down resulted in a significant decrease in the trimethyl-K27 level but had little affect on the trimethyl-K9 level (FIG. 5C, third and fourth panels). Unexpectedly, an increase in monomethyl-K27 and a moderate decrease in dimethyl-K27 were also observed (FIG. 5C, the top two panels). The fact that SUZ12 knock-down did not affect EZH2 level (FIG. 5A), in combination with the requirement of SUZ12 for histone H3-K27 methyltransferase activity in vitro (FIG. 3B), indicates that SUZ12 directly contributes to histone H3-K27 methylation.

EXAMPLE 7

SUZ12-Mediated Silencing of the EED-EZH2 Complex

Figure 6A:
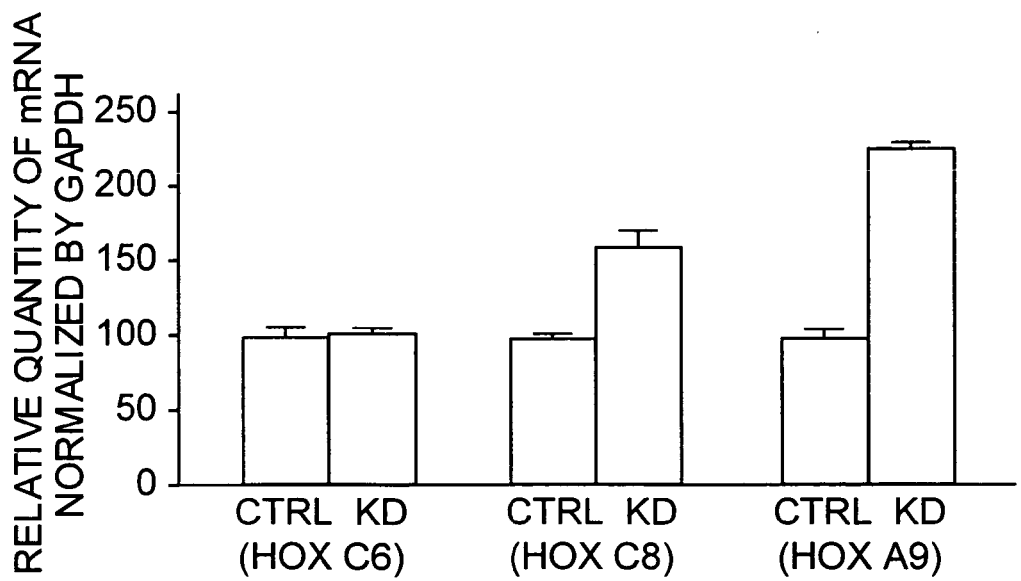
FIGS. 6A through 6B indicate that SUZ12 knock-down results in derepression of Hox gene expression and decreased levels of H3-K27 methylation on the HoxA9 gene.

Studies in Drosophila have established a role for histone H3-K27 methylation in Hox gene silencing (Cao, et al. (2002) Science 298:1039-1043; Muller, et al. (2002) Cell 111:197-208). Data presented herein indicate that SUZ12 is important for histone H3-K27 methylation in vitro and in vivo. To determine whether histone H3-K27 methylation is involved in Hox gene silencing in mammalian cells, like that in Drosophila, expression of EED-EZH2 target genes in the SUZ12 knock-down cells was evaluated. The expression level of several Hox genes, including HoxC6, HoxC8, and HoxA9 in the knock-down cells and the parallel control cells were examined by real-time RT-PCR. Results shown in FIG. 6A demonstrate that SUZ12 knock-down resulted in derepression of HoxC8 and HoxA9 but had little effect on HoxC6.

Figure 6B:
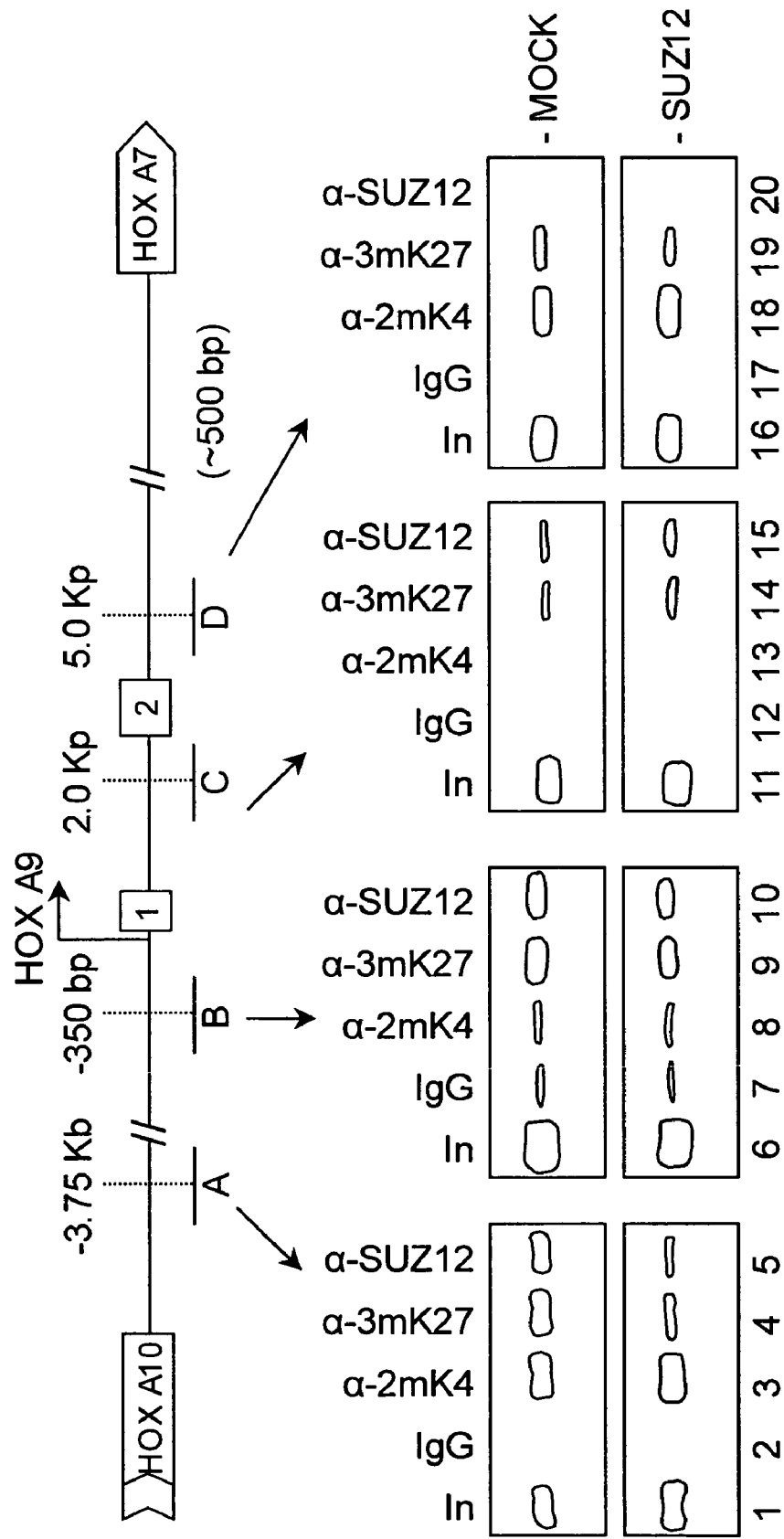

As SUZ12 knock-down had a dramatic effect on HoxA9, the relationship between SUZ12 knock-down, histone H3-K27 methylation, and HoxA9 derepression were examined. Accordingly, SUZ12 binding and histone H3-K27 methylation, at different locations of the human HoxA9 gene, were analyzed by chromatin immunoprecipitation (ChIP) using antibodies against SUZ12 and trimethyl-K27. As controls for the ChIP assays and for antibody specificity, equal amounts of IgG and anti-histone H3-dimethyl-K4 antibodies were included. Representative regions that covered the promoter (B), intron (C), and downstream (D) of the gene were analyzed. In addition, a region (A) about 4-kb upstream of the transcription initiation site, which shows a high degree of sequence homology between human and mouse genes, was also analyzed. Results shown in FIG. 6B indicate that SUZ12 and 3mK27 were present preferentially in regions A (lanes 4 and 5) and B (lanes 9 and 10) when compared with that present in regions C (lanes 14 and 15) and D (lanes 19 and 20) in the mock knock-down cells (top panels). Consistent with a role for SUZ12 in histone H3-K27 methylation, knock-down SUZ12 resulted in a significant decrease in SUZ12 binding, concomitant with a loss of histone H3-3mK27 in regions A and B, particularly in region A (FIG. 6B, lanes 4 and 5, compare top and bottom panels). As three YY1 binding sites were identified in region A, this region may have functions similar to that of the Drosophila Polycomb responsive element (PRE). Therefore, loss of direct SUZ12 binding correlates with a loss of histone H3-K27 methylation and derepression of the HoxA9. Very little change in histone H3-K4 methylation, believed to be a marker for gene activation, was observed. Collectively, the data indicate that SUZ12 is critical for the enzymatic activity and silencing function of the EED-EZH2 complex.

EXAMPLE 8

Inhibitors of Reconstituted EED-EZH2 Complex

Histone substrate was coated in the wells of a 96-well plate and reaction mixture containing reconstituted EED-EZH2 complex and a test compound were added to the wells (FIG. 7A). The wells were washed, H3-mK antibody was added, and ELISA was performed to determine whether the test compound inhibited the HMTase activity of the reconstituted complex. In this primary screen, 22 of 20,000 compounds screened, exhibited inhibitory activity. The 22 compounds were further tested for specificity to the reconstituted EED-EZH2 complex as compared to other HMTases.

The foregoing is illustrative of the present invention, and is not to be construed as limiting thereof. The invention is defined by the following claims, with equivalents of the claims to be included therein.

That which is claimed is:

1. A method of identifying a compound that inhibits the histone methyltransferase (HMTase) activity for lysine 27 of histone H3 (H3-K27) of a reconstituted complex comprising mammalian Embryonic Ectoderm Development (FED), Enhancer of Zeste Homolog 2 (EZH2), and Suppressor of Zeste 12 (SUZ12), wherein the reconstituted complex has H3-K27 HMTase activity, the method comprising:
   contacting the reconstituted complex with a histone substrate in the presence of a test compound; and
   detecting the level of H3-K27 methylation under conditions sufficient to provide H3-K27 methylation, wherein a reduction in H3-K27 methylation as compared with the level of H3-K27 methylation in the absence of the test compound indicates that the test compound is an inhibitor of the H3-K27 HMTase activity of the reconstituted complex.

2. The method of claim 1, wherein the reconstituted complex further comprises mammalian RbAp48, AEBP2 or both.

3. The method of claim 1, wherein the histone substrate is a core histone, a histone octamer, a mononucleosome, a dinucleosome or an oligonucleosome.

4. The method of claim 1, wherein the histone substrate is a dinucleosome.

5. The method of claim 1, wherein the method is a cell-based method.

6. The method of claim 1, wherein the method is a cell-free method.

7. A method of identifying a candidate compound for treating cancer, comprising:
   contacting a reconstituted complex comprising mammalian Embryonic Ectoderm Development (EED), Enhancer of Zeste Homolog 2 (EZH2) and Suppressor of Zeste 12 (SUZ12) with a histone substrate in the presence of a test compound;
   wherein the reconstituted complex has histone methyltransferase (HMTase) activity for lysine 27 of histone H3 (H3-K27); and
   detecting the level of histone methylation of H3-K27 under conditions sufficient to provide H3-K27methylation, wherein a reduction in H3-K27 methylation as compared with the level of H3-K27 methylation in the absence of the test compound indicates that the test compound is a candidate compound for the treatment of cancer.

8. The method of claim 7, wherein the reconstituted complex further comprises mammalian RbAp48, AEBP2 or both.

9. The method of claim 1, wherein at least one of the proteins in the complex is a fusion protein comprising a purification tag.

10. The method of claim 7, wherein at least one of the proteins in the complex is a fusion protein comprising a purification tag.

11. The method of claim 7, wherein the histone substrate is a core histone, a histone octamer, a mononucleosome, a dinucleosome or an oligonucleosome.

12. The method of claim 7, wherein the method is a cell-based method.

13. The method of claim 7, wherein the method is a cell-free method.

14. A method of identifying a compound that inhibits the histone methyltransferase (HMTase) activity for lysine 27 of histone H3 (H3-K27) of a reconstituted complex comprising human Embryonic Ectoderm Development (EED), Enhancer of Zeste Homolog 2 (EZH2), and Suppressor of Zeste 12 (SUZ12), wherein the reconstituted complex has H3-K27 HMTase activity, the method comprising:
   contacting the reconstituted complex with a histone substrate in the presence of a test compound; and
   detecting the level of H3-K27 methylation under conditions sufficient to provide H3-K27 methylation, wherein a reduction in H3-K27 methylation as compared with the level of H3-K27 methylation in the absence of the test compound indicates that the test compound is an inhibitor of the H3-K27 HMTase activity of the reconstituted complex.

15. A method of identifying a candidate compound for treating cancer, comprising:
   contacting a reconstituted complex comprising human Embryonic Ectoderm Development (EED), Enhancer of Zeste Homolog 2 (EZH2) and Suppressor of Zeste 12 (SUZ12) with a histone substrate in the presence of a test compound;
   wherein the reconstituted complex has histone methyltransferase (HMTase) activity for lysine 27 of histone H3 (H3-K27); and
   detecting the level of histone methylation of H3-K27 under conditions sufficient to provide H3-K27 methylation, wherein a reduction in H3-K27 methylation as compared with the level of H3-K27 methylation in the absence of the test compound indicates that the test compound is a candidate compound for the treatment of cancer.

* * * * *

UNITED STATES PATENT AND TRADEMARK OFFICE
CERTIFICATE OF CORRECTION

PATENT NO. : 7,563,589 B2  
APPLICATION NO. : 11/140659  
DATED : July 21, 2009  
INVENTOR(S) : Zhang et al.

Page 1 of 1

It is certified that error appears in the above-identified patent and that said Letters Patent is hereby corrected as shown below:

In the Claims
Column 31, Claim 1, Line 43: Please correct this claim by deleting "(FED)" and replacing it with -- (EED) --.

Column 32, Claim 9, Lines 21-22: Please correct claim by deleting "comprising a purification tag".

Column 32, Claim 10, Lines 24-25: Please correct claim by deleting "comprising a purification tag".

Signed and Sealed this

Twenty-ninth Day of September, 2009

David J. Kappos
*Director of the United States Patent and Trademark Office*